United States Patent
Benecke et al.

(10) Patent No.: US 10,131,616 B2
(45) Date of Patent: Nov. 20, 2018

(54) LUBRICANT COMPOSITION OF MATTER AND METHODS OF PREPARATION

(71) Applicant: PETROLIAM NASIONAL BERHAD, Kuala Lumpur (MY)

(72) Inventors: Herman Paul Benecke, Columbus, OH (US); Daniel B. Garbark, Blacklick, OH (US)

(73) Assignee: Petroliam Nasional Berhad, Kuala Lumpur (MY)

( * ) Notice: Subject to any disclaimer, the term of this patent is extended or adjusted under 35 U.S.C. 154(b) by 867 days.

(21) Appl. No.: 14/381,545

(22) PCT Filed: Feb. 28, 2013

(86) PCT No.: PCT/MY2013/000040
§ 371 (c)(1),
(2) Date: Aug. 27, 2014

(87) PCT Pub. No.: WO2013/129909
PCT Pub. Date: Sep. 6, 2013

(65) Prior Publication Data
US 2015/0018260 A1    Jan. 15, 2015

Related U.S. Application Data

(60) Provisional application No. 61/604,301, filed on Feb. 28, 2012.

(51) Int. Cl.
*C10M 105/38* (2006.01)
*C07C 67/40* (2006.01)
(Continued)

(52) U.S. Cl.
CPC ............. *C07C 67/40* (2013.01); *C07C 51/34* (2013.01); *C07C 67/08* (2013.01); *C10M 105/38* (2013.01);
(Continued)

(58) Field of Classification Search
CPC .............................................. C10M 2207/282
(Continued)

(56) References Cited

U.S. PATENT DOCUMENTS

| 667,043 A | 1/1901 | Steep |
|---|---|---|
| 2,401,338 A | 6/1946 | Dunmire |

(Continued)

FOREIGN PATENT DOCUMENTS

| AU | 165032 | 2/1954 |
|---|---|---|
| CN | 101077856 A | 11/2007 |

(Continued)

OTHER PUBLICATIONS

Office Action for U.S. Appl. No. 14/381,530 dated Dec. 10, 2015.
(Continued)

*Primary Examiner* — Vishal V Vasisth
(74) *Attorney, Agent, or Firm* — LeClairRyan PLLC

(57) ABSTRACT

Ester polyol esters are a unique class of lubricants that have adjustable molecular weights, viscosities, and pour points based on the character of their reaction materials and relative ratios. There is provided a method for preparing at least one ester polyol ester, the method comprising esterifying an ester polyol reaction mixture to produce ester polyol, the reaction mixture comprising an ozone acid mixture and at least one primary polyol, wherein the ozone acid mixture comprises at least one dicarboxylic acid and at least one monocarboxylic acid; and capping the ester polyol with at least one capping carboxylic acid to produce ester polyol ester.

24 Claims, 10 Drawing Sheets

Preparation of Polyol Esters

TMP Trioleate

(51) Int. Cl.
C10M 105/42 (2006.01)
C07C 67/08 (2006.01)
C11C 1/00 (2006.01)
C11C 1/04 (2006.01)
C11C 3/00 (2006.01)
C11C 3/02 (2006.01)
C07C 51/34 (2006.01)

(52) U.S. Cl.
CPC ........... *C10M 105/42* (2013.01); *C11C 1/005* (2013.01); *C11C 1/04* (2013.01); *C11C 3/00* (2013.01); *C11C 3/006* (2013.01); *C11C 3/02* (2013.01); *C10M 2207/301* (2013.01); *C10N 2220/021* (2013.01); *C10N 2220/022* (2013.01); *C10N 2220/027* (2013.01); *C10N 2220/028* (2013.01); *C10N 2230/02* (2013.01); *C10N 2230/26* (2013.01); *C10N 2270/00* (2013.01)

(58) Field of Classification Search
USPC ........................................................ 508/492
See application file for complete search history.

(56) References Cited

U.S. PATENT DOCUMENTS

| | | | |
|---|---|---|---|
| 2,566,559 | A | 9/1951 | Dolnick et al. |
| 2,813,113 | A | 11/1957 | Goebel et al. |
| 2,997,493 | A | 8/1961 | Huber |
| 3,048,608 | A | 8/1962 | Girard et al. |
| 4,061,581 | A | 12/1977 | Leleu et al. |
| 4,298,730 | A | 11/1981 | Galleymore et al. |
| 4,313,890 | A | 2/1982 | Chu et al. |
| 4,865,879 | A | 9/1989 | Finlay |
| 5,736,748 | A | 4/1998 | Lysenko et al. |
| 5,773,256 | A | 6/1998 | Pelenc et al. |
| 5,773,391 | A | 6/1998 | Lawate et al. |
| 6,107,500 | A | 8/2000 | Prossel et al. |
| 6,362,368 | B1 | 3/2002 | Frische et al. |
| 7,125,950 | B2 | 10/2006 | Dwan'Isa et al. |
| 7,192,457 | B2 | 3/2007 | Murphy et al. |
| 7,241,914 | B2 | 7/2007 | Wartini et al. |
| 7,589,222 | B2 | 9/2009 | Narayan et al. |
| 2004/0167343 | A1 | 8/2004 | Halpern et al. |
| 2005/0112267 | A1 | 5/2005 | Kian et al. |
| 2006/0194974 | A1 | 8/2006 | Narayan et al. |
| 2009/0216040 | A1 | 8/2009 | Benecke et al. |
| 2009/0239964 | A1 | 9/2009 | Sasaki et al. |
| 2010/0087350 | A1 | 4/2010 | Sonnenschein et al. |
| 2010/0117022 | A1 | 5/2010 | Carr et al. |
| 2011/0077350 | A1 | 3/2011 | Malotky et al. |
| 2011/0269979 | A1 | 11/2011 | Benecke et al. |
| 2011/0269981 | A1 | 11/2011 | Benecke et al. |
| 2011/0269982 | A1 | 11/2011 | Benecke et al. |
| 2012/0184758 | A1 | 7/2012 | Krull et al. |
| 2015/0005520 | A1 | 1/2015 | Benecke et al. |
| 2015/0018444 | A1 | 1/2015 | Garbark et al. |
| 2015/0018620 | A1 | 1/2015 | Oneda et al. |
| 2015/0080599 | A1 | 3/2015 | Garbark et al. |
| 2015/0087850 | A1 | 3/2015 | Benecke et al. |

FOREIGN PATENT DOCUMENTS

| | | |
|---|---|---|
| CN | 101195577 A | 6/2008 |
| CN | 201343513 Y | 11/2009 |
| CN | 101812349 A | 8/2010 |
| CN | 101899160 A | 12/2010 |
| CN | 102010772 A | 4/2011 |
| EP | 0010333 A1 | 4/1980 |
| EP | 1260497 A2 | 11/2002 |
| EP | 1529828 A1 | 5/2005 |
| EP | 1533360 A1 | 5/2005 |
| GB | 915461 | 1/1963 |
| JP | S57185235 A | 11/1982 |
| JP | 04018049 A | 1/1992 |
| JP | 2008013546 A | 1/2008 |
| KR | 10-2008-0023290 A | 3/2008 |
| MY | 140833 A | 1/2010 |
| WO | 1993024585 A1 | 12/1993 |
| WO | 98/50338 A1 | 11/1998 |
| WO | 2000039068 A1 | 7/2000 |
| WO | 2004087847 A1 | 10/2004 |
| WO | 2006-093874 A2 | 9/2006 |
| WO | 2006093874 A2 | 9/2006 |
| WO | 2007-027223 A2 | 3/2007 |
| WO | 2007027223 A2 | 3/2007 |
| WO | 2010-078505 A1 | 7/2010 |
| WO | 2010/085545 A1 | 7/2010 |
| WO | 2010078491 A1 | 7/2010 |
| WO | 2010078493 A1 | 7/2010 |
| WO | 2010078498 A1 | 7/2010 |
| WO | 2010078505 A1 | 7/2010 |
| WO | 2013129907 A1 | 9/2013 |
| WO | 2013129908 A1 | 9/2013 |
| WO | 2013129909 A1 | 9/2013 |
| WO | 2013129910 A1 | 9/2013 |
| WO | 2013129911 A1 | 9/2013 |
| WO | 2014133380 A8 | 9/2014 |

OTHER PUBLICATIONS

Gmehling et al., "Azeotropic Data for Binary Mixtures", Handbook of Chemistry and Physics (96th Edition, 2015-2016), pp. 6-210 to 6-228.
Sebedio et al., "Comparison of the Reaction Products of Oleic Acid Ozonized in BCl3-, HCl- and BF3—MeOH Media," Chemistry and Physics of Lipids 35(1):21-28 (1984) (Abstract only).
Akerman et al., "Biolubricant Synthesis Using Immobilised Lipase: Process Optimisation of Trimethylolpropane Oleate Production," Process Biochem. 46:2225-2231 (2011).
Translated Office Action for corresponding Chinese Application No. 201380022561.5, dated Sep. 6, 2015.
Search Report and Written Opinion for Singapore Application No. 11201405261T, dated Sep. 10, 2015.
Search Report and Written Opinion for corresponding Singapore Application No. 11201405268P, dated Oct. 1, 2015.
Office Action for China Application No. 201380022561.5 (dated Apr. 18, 2016).
International Search Report and Written Opinion for PCT/MY2013/000040 dated Jun. 28, 2013.
Ackman et al., "Ozonolysis of Unsaturated Fatty Acids. I. Ozonolysis of Oleic Acid," Can. J. Chem., 39:1956-1963 (1961).
Yunus et al., "Preparation and Characterization of Trimethylolpropane Esters from Palm Kernel Oil Methyl Esters," J. Oil Palm Research, 15(2):42-49 (2003).
Spyros, A., "Quantitative Determination of the Distribution of Free Hydroxylic and Carboxylic Groups in Unsaturated Polyester and Alkyd Resins by 31 P-NMR Spectroscopy," J. Appl. Polym. Sci., 83:1635-1642 (2002).
PCT International Search Report and Written Opinion for International Patent Application No. PCT/MY2013/000038 (dated Jun. 27, 2013).
PCT International Search Report and Written Opinion for International Patent Application No. PCT/MY2013/000039 (dated Jun. 27, 2013).
PCT International Search Report and Written Opinion for International Patent Application No. PCT/MY2013/000040 (dated Jun. 28, 2013).
PCT International Search Report and Written Opinion for International Patent Application No. PCT/MY2013/000041 (dated Jun. 28, 2013).
PCT International Search Report and Written Opinion for International Patent Application No. PCT/MY2013/000042 (dated Jun. 28, 2013).
International Preliminary Report on Patentability for International Patent Application No. PCT/MY2013/000038 (dated Sep. 12, 2014).
International Preliminary Report on Patentability for International Patent Application No. PCT/MY2013/000039 (dated Sep. 12, 2014).

(56) References Cited

OTHER PUBLICATIONS

International Preliminary Report on Patentability for International Patent Application No. PCT/MY2013/000040 (dated Sep. 12, 2014).
International Preliminary Report on Patentability for International Patent Application No. PCT/MY2013/000041 (dated Sep. 12, 2014).
International Preliminary Report on Patentability for International Patent Application No. PCT/MY2013/000042 (dated Sep. 12, 2014).
Third Party Submission for U.S. Appl. No. 14/381,554 dated Jul. 13, 2015.
Extended European Search Report for EP13755362.4 dated Aug. 21, 2015.
Extended European Search Report for EP13754711.3 dated Sep. 3, 2015.
PCT International Search Report and Written Opinion corresponding to PCT/MY2014/000026, Feb. 28, 2014(dated May 21, 2014).
Office Action for U.S. Appl. No. 14/381,539 dated May 29, 2015.
Translated Office Action for CN 201380022561.5 dated Oct. 8, 2016.
Translated Office Action for JP 2014-559853 dated Jul. 11, 2016.
Office Action for EP 13754711.3 dated Dec. 9, 2016.
Office Action for U.S. Appl. No. 14/381,554 dated Aug. 2, 2016.
Office Action for U.S. Appl. No. 14/381,564, dated Jun. 3, 2015.
Office Action for U.S. Appl. No. 14/771,137 dated Jan. 11, 2016.
Office Action for U.S. Appl. No. 14/771,137 dated Oct. 12, 2016.
Office Action for U.S. Appl. No. 14/381,554 dated May 3, 2017.

Specific Oxidation Acids formed by Oxidative Cleavage of Fatty Acids (Note that malonic acid will undergo decarboxylation to form acetic acid and carbon dioxide under oxidative ozonolysis conditions)

Polyol Ester Polyol Viscosities versus DMR at HCR of 1.25 after Capping with Nonanoic Acid Polyol Ester Polyol Viscosities versus HCR at DMR of 0.11-0.12 after Capping with Nonanoic Acid Combined DMR and HCR Required to Obtain ISO 49-58 cS Hydraulic Fluids One-stage Synthesis Approach of Producing an Ester Polyol Ester for Lubricant Base Oil

LUBRICANT COMPOSITION OF MATTER AND METHODS OF PREPARATION

This application is a national stage application under 35 U.S.C. 371 from PCT/MY2013/000040, filed Feb. 28, 2013, which claims the benefit of U.S. Provisional Patent Application Ser. No. 61/604,301, filed Feb. 28, 2012, each of which is hereby incorporated by reference in its entirety.

FIELD OF THE INVENTION

The present invention relates to methods for the preparation of ester polyol esters for lubricant application. In particular, the ester polyol esters are prepared from the esterification reaction between ozone acids, typically derived from oxidative ozonolysis of fatty acids, and at least one primary polyol, such as trimethylolpropane (TMP) or glycerin. The resulting ester polyols produced from these reactions are then esterified with selected monoacid(s) to produce desired ester polyol esters. The ester polyol esters prepared in the present invention are particularly useful for use as synthetic base stock for lubricant applications.

BACKGROUND OF THE INVENTION

The listing or discussion of an apparently prior-published document in this specification should not necessarily be taken as an acknowledgement that the document is part of the state of the art or is common general knowledge.

The present invention is directed to a process to produce ester polyol esters (EPE) using renewable resources such as oils and fats, fatty acids, and fatty acid esters derived from plant and animal resources. These ester polyol esters are classified as Group V synthetic lubricant base stock and are particularly useful for use in high performance lubricant applications.

Group V lubricant base stocks include ester compounds and one type of high performance esters are polyol esters (PE) which are prepared by complete esterification of polyols such as TMP with monoacids. TMP trioleate is a common polyol ester formed from the esterification of the polyol TMP with oleic acid. Although Group V lubricant base stock technologies have demonstrated several performance advantages over traditional mineral oils, there is still room for further advancement or improvement in this field, especially with respect to enhancing performance characteristics of base stocks to extend the lubricant drain interval in high performance lubricant applications.

One of the common disadvantages of the commercially available polyol esters is related to high pour points, especially polyol esters produced from saturated fatty acids derived from tropical resources such as palm or coconut. Another disadvantage limiting performance is associated with the level of unsaturation where the double bonds in fatty acid components of polyol esters provide a point of attack for oxidation reactions to take place, which encourages oil degradation and precludes them for use in certain lubricant applications.

WO 2010/078505 discusses the preparation of ester polyols where the fatty acids derived from vegetable and/or animal oils are initially subjected to oxidative cleavage using ozone as the preferred cleavage reagent so that all double bonds are cleaved in a manner to generate carboxylic acid groups at each original double bonded carbon atom. In the oxidative ozonolysis of fatty acids derived from either vegetable oils or animal fats, a mixture of diacids and monoacids (referred to as ozone acids) are produced. The ozone acids are then esterified with select primary polyols such as TMP and/or other primary polyols to produce a wide range of polyol esters having a certain range of molecular weight and hydroxyl values.

In U.S. Pre-Grant Publication No. 2005/0112267, Yeong et al. concluded that common palm-based materials, especially palm olein or their ester derivatives developed for hydraulic application are only suitable for use in a tropical climate with temperatures ranging from 15° C. to 40° C. due to their low pour point.

The paper "Preparation and Characterization of Trimethylolpropane Esters from Palm Kernel Oil Methyl Esters" (Robiah et al., *Journal of Oil Palm Research*, 15(2), December 2003, pp. 42-49) reported that a lubricant base stock, i.e., TMP esters having an improved pour point in the range of 1° C. had been prepared from palm oil methyl ester (POME) and palm kernel oil methyl ester (PKOME). This improvement reflects that lubricant formulated with such esters can be used at a much lower temperature condition than reported previously. Malaysian Patent No. 140833 also filed by Robiah et al. discusses that the pour point of the TMP esters for the lubricant application can be reduced to a level of around −35° C. by removing via fractionation some of the saturated components in the ester mix. However, this separation step does not adequately remove all of the saturates to meet the most stringent requirement for pour point accepted by industry or original equipment manufacturers (OEMs).

SUMMARY OF THE INVENTION

The present inventors have addressed the problems in the art and prepared ester polyol esters (EPE) particularly useful for use as synthetic base stock for lubricant applications.

In particular, the present invention relates to a unique method of preparing ester polyols (EP) and ester polyol esters (EPE) and products therefrom.

In particular, according to an aspect of the invention, ozone acids which may be obtained through oxidative ozonolysis of fatty acids are esterified with at least one primary polyol, for example, trimethylolpropane (TMP), or other primary polyols to generate intermediate ester polyols (EP). These ester polyols are then esterified with at least one carboxylic acid to produce ester polyol esters (EPE) having unique properties suited for lubricant base stock applications.

Accordingly, the present invention provides a method for preparing at least one ester polyol ester, the method comprising:

esterifying an ester polyol reaction mixture to produce ester polyol, the reaction mixture comprising an ozone acid mixture and at least one primary polyol, wherein the ozone acid mixture comprises at least one dicarboxylic acid and at least one monocarboxylic acid; and capping the ester polyol with at least one capping carboxylic acid to produce ester polyol ester.

In the method according to the invention,
(i) the ozone acid mixture may have a Difunctional/Monofunctional Ratio (DMR) corresponding to a ratio of moles of dicarboxylic acid to moles of monocarboxylic acid; and the ester polyol ester has a viscosity proportional to the DMR of the ozone acid mixture; and/or
(ii) the ester polyol reaction mixture may have a hydroxyl to carboxyl ratio (HCR) corresponding to a ratio of moles of —OH groups to moles of —COOH groups and the ester polyol ester has a viscosity inversely proportional to the HCR of the ester polyol reaction mixture.

In one particular aspect of the invention, there is provided a method for preparing an ester polyol ester, the method comprising esterifying an ozone acid mixture comprising at least one monocarboxylic acid and at least one dicarboxylic acid, in the presence of at least one primary polyol The ozone acid mixture according to any aspect of the invention may be prepared by reacting at least one fatty acid with ozone followed by oxidation. The oxidation may be with oxygen.

In any aspect of the invention, the ozone acid mixture may comprise at least one dicarboxylic acid and at least one first monocarboxylic acid; and the method may comprise adding at least one additional second monocarboxylic acid to the ozone acid mixture, wherein the first and second monocarboxylic acids may be different. The addition of the one or more additional second monocarboxylic acid may reduce the Difunctional/Monofunctional Ratio (DMR) of the ozone acid mixture.

In one particular aspect of the invention, the at least one capping carboxylic acid may be one or more monocarboxylic acids. More in particular, the at least one capping carboxylic acid may be selected from the group consisting of: acetic, propanoic, butyric, pentanoic, hexanoic, nonanoic, 2-ethyl hexanoic, heptanoic, octanoic acid, decanoic, lauric, myristic, palmitic and stearic acids, and mixtures thereof. More in particular, the at least one capping carboxylic acid may be nonanoic acid.

The primary polyol according to any aspect of the invention may be selected from glycerin, diglycerin, ethylene glycol, diethylene glycol, 1,2-propanediol, bis(1,2-propanediol), 2-methyl-1,3-propanediol (2-MePG), trimethylolpropane (TMP), di-trimethylolpropane (Di-TMP), neopentyl glycol (NPG), pentaerythritol (PE), dipentaerythritol (diPE) and sorbitol. More in particular, the primary polyol may be a branched polyhydric primary polyol. More in particular, the primary polyol may be trimethylolpropane (TMP).

The at least one fatty acid according to any aspect of the invention may be produced by hydrolyzing at least one triglyceride. More in particular, the at least one triglyceride may comprise at least one vegetable oil and/or at least one animal fat.

According to one aspect, the present invention provides an ester polyol ester obtained or obtainable by the above methods According to one aspect, the present invention provides an ester polyol ester lubricant base oil comprising the ester polyol ester obtained or obtainable by the above methods According to one aspect, the present invention provides an ester polyol ester lubricant base oil comprising the reaction product of at least one carboxylic acid and at least one ester polyol, wherein the ester polyol may have at least one ester group, a first hydroxyl group, and at least a second hydroxyl group.

According to one aspect, the present invention provides an ester polyol ester composition comprising a compound of Formula I:

wherein R1 is a linear or branched alkyl chain having from 1 to 17 carbon atoms, optionally substituted with one or more hydroxyl groups, or R1 is a linear alkyl chain with from 2 to 18 carbon atoms and a terminal carboxylic acid group which is optionally esterified with a polyol compound of formula R2-OH;

R2, when attached to a hydroxyl group, is a linear or branched primary polyol having from 2 to 12 carbon atoms, wherein each alcohol functional group is optionally esterified with a monocarboxylic acid or dicarboxylic acid of formula R1-COOH, or a monocarboxylic acid of formula R3-COOH; and R3 is a linear or branched alkyl chain having from 1 to 17 carbon atoms, optionally substituted with one or more hydroxyl groups.

According to one aspect, the present invention provides an ester polyol ester composition comprising a compound of Formula II:

wherein R4 is the alkyl chain of a monocarboxylic acid selected from the group consisting of: acetic, propanoic, butyric, pentanoic, hexanoic, nonanoic, 2-ethyl hexanoic, heptanoic, octanoic acid, decanoic, lauric, myristic, palmitic and stearic acids, or R4 is a C2-C18 linear alkyl chain with a terminal carboxylic acid group which is optionally esterified with a polyol compound of formula R5-OH;

R5, when attached to a hydroxyl group, is the alkyl chain of a primary polyol selected from the group consisting of: glycerin, diglycerin, ethylene glycol, diethylene glycol, 1,2-propanediol, bis(1,2-propanediol), 2-methyl-1,3-propanediol (2-MePG), trimethylolpropane (TMP), di-trimethylolpropane (Di-TMP), neopentyl glycol (NPG), pentaerythritol (PE), dipentaerythritol (diPE) and sorbitol, wherein each alcohol functional group is optionally esterified with a monocarboxylic acid or dicarboxylic acid of formula R4-COOH, or a monocarboxylic acid of formula R6-COOH; and R6 is the alkyl chain of a monocarboxylic acid selected from the group consisting of: acetic, propanoic, butyric, pentanoic, hexanoic, nonanoic, 2-ethyl hexanoic, heptanoic, octanoic acid, decanoic, lauric, myristic, palmitic and stearic acids.

According to one aspect, the present invention provides an ester polyol ester composition comprising a compound of Formula III:

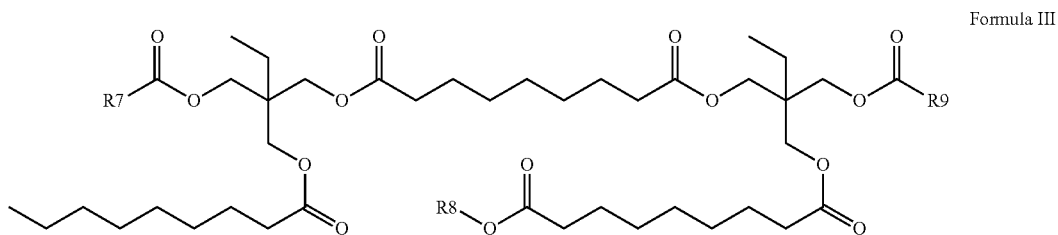

Formula III wherein R7, R8 and R9 are independently:
a linear or branched alkyl chain of between 1 to 17 carbon atoms, optionally substituted with one or more hydroxyl groups;
a C2-C18 linear alkyl chain with a terminal carboxylic acid group which is optionally esterified with a polyol compound of formula R10-OH; or
R10, wherein R10, when attached to a hydroxyl group, is a linear or branched primary polyol having from 2 to 12 carbon atoms and each alcohol functional group in R10 is optionally esterified with a linear or branched monocarboxylic acid having from 2 to 18 carbon atoms, or a dicarboxylic acid having from 3 to 9 carbon atoms.

According to one aspect, the present invention provides an ester polyol ester composition comprising a compound of Formula IV:

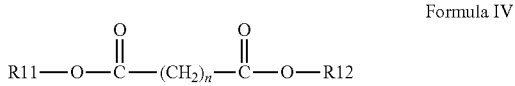

Formula IV wherein n is from 0 to 16;
R11 and R12, when each attached to a hydroxyl group, are independently a linear or branched primary polyol having from 2 to 12 carbon atoms, wherein each alcohol functional group is optionally esterified with a monocarboxylic acid of formula R13-COOH or dicarboxylic acid of formula R14-COOH;
R13 is a linear or branched alkyl chain having from 1 to 17 carbon atoms, optionally substituted with one or more hydroxyl groups; and
R14 is a C2-C18 linear alkyl chain with a terminal carboxylic acid group which is optionally esterified with a primary polyol compound of formula R11-OH or R12-OH.

According to one aspect, the present invention provides an ester polyol ester composition comprising an azelaic acid ester polyol ester wherein azelaic acid is esterified with at least one polyol of formula R15-OH; wherein each polyol R15-OH is a linear or branched primary polyol having from 2 to 12 carbon atoms and contains at least two alcohol functional groups which are independently optionally esterified with a carboxylic acid of formula R16-COOH; and R16 is chosen from the group consisting of: a linear or branched alkyl chain having from 1 to 17 carbon atoms, optionally substituted with one or more hydroxyl groups; and a C2-C18 linear alkyl chain with a terminal carboxylic acid group which is optionally esterified with a polyol compound of formula R15-OH.

The Difunctional/Monofunctional ratio (DMR) of the ozone acids plus additional monoacids may be from about 0.05 to about 0.71. The carboxylic acid may have a hydroxyl to carboxyl ratio (HCR) corresponding to a ratio of moles of —OH groups to moles of —COOH groups and is from about 1.0 to about 2.0. The ester polyol ester may have a viscosity proportional to the Difunctional/Monofunctional Ratio (DMR) of ozone acids, and the viscosity at 40° C. of the ester polyol ester may be from about 7.14 cSt to about 97.08 cSt. The molecular weight (GPC) of the ester polyol ester may be from about 700 g/mol to about 2000 g/mol.

In the method of the invention, in the step of esterifying the ozone acids, the at least one primary polyol is added in excess to produce ester polyol. The esterification may further comprise adding at least one monoacid to produce ester polyol.

According to a particular aspect, the method according to any aspect of the invention may further comprise:
capping the ester polyol with Nonanoic acid to form the ester polyol ester,
wherein the Difunctional/Monofunctional ratio (DMR) of the mixture of ozone acids plus additional monoacids is about 1.25,
the viscosity at 40° C. of the ester polyol ester is from about 37.7 (cSt) to about 61.6 (cSt), and
the ester polyol ester has a pour point from about −57.0° C. to about −42.0° C.

The fatty acids used in the present invention may be in the form of a plurality or a mixture of fatty acids. In particular, the fatty acids may be derived from a mixture of fractionated palm fatty acid distillate (PFAD) and/or palm kernel fatty acid distillate The primary polyol may be a branched polyhydric primary polyol. The primary polyol may be selected from glycerin; 1,2-propanediol; 2-methyl-1,3-propanediol (2-MePG); trimethylolpropane (TMP); di-trimethylolpropane (Di-TMP); neopentyl glycol (NPG); pentaerythritol (PE); dipentaerythritol (diPE); and sorbitol. In particular, the primary polyol may be trimethylolpropane (TMP).

The at least one monoacid may be selected from the group consisting of: hexanoic, nonanoic, 2-ethyl hexanoic, heptanoic, and octanoic acid.

Selective DMR and HCR ratios may influence the properties of lubricant base stock. For example, an increased ratio of DMR results in increased molecular weight causing an increased viscosity and decreased volatility. An increased ratio of HCR results in decreased molecular weight causing a decrease in viscosity and increase in volatility.

According to another aspect of the invention there is also provided a one-step method for forming an ester polyol ester, comprising esterifying an ozone acid mixture comprising at least one monocarboxylic acid and at least one dicarboxylic acid in the presence of at least one primary polyol to produce the ester polyol ester. Esterifying the ozone acids with at least one primary polyol may comprise adding at least one monoacid to produce ester polyol esters.

There is also provided an ester polyol ester obtainable or obtained according to any method to the invention. There is also provided an ester polyol ester lubricant base oil comprising the ester polyol ester according to the invention.

According to another aspect, there is provided an ester polyol ester lubricant base oil, comprising the reaction product of:
at least one carboxylic acid; and
at least one ester polyol,
wherein the ester polyol has at least one ester group, a first hydroxyl group, and at least a second hydroxyl group, The ester polyol ester lubricant base oil according to any aspect of the invention having a pour point of between −57.0 to −15.0° C.

The ester polyol esters of the present invention are unique because they have lower pour points than pour points of typical biobased lubricant basestocks within the same viscosity range. This invention also provides a means to produce a broader range of kinematic viscosity profiles at 40° C. ranging from 15 cSt to 200 cSt, while maintaining an appreciably lower volatility, which indirectly reflects good thermal stability. Low pour points may eliminate or reduce the need for pour point depressants (PPDs), while the broader viscosity profiles will minimize or eliminate the need of adding polymeric viscosity modifiers in lubricant formulations. These advantages will greatly broaden the applicability of ester polyol esters.

The structures of the ester polyol esters of the present invention are also different than the conventional polyol esters, and this structural uniqueness is transferred to performance advantages. The structural distinctiveness can be related to the unsymmetrical arrangement of their molecular structure where different proportions of diacid and/or monoacids react with any one primary polyols during esterification. The resulting diversity of structures hinders close packing of the polyol ester chains and thus inhibits crystallization. This is another advantage with respect to maintaining the ester polyol ester fluidity, especially when preparing the polyols from tropical feedstock, such as, palm or coconut that contain high amounts of high melting palmitic and stearic acids.

BRIEF DESCRIPTION OF THE FIGURES

The accompanying figures, which are incorporated in and constitute a part of this specification, illustrate aspects of the invention and, together with a general description of the invention given above, and the detailed description given below, serve to explain the invention.

DETAILED DESCRIPTION OF THE INVENTION

Bibliographic references mentioned in the present specification are for convenience listed in the form of a list of references and added at the end of the examples. The whole content of such bibliographic references is herein incorporated by reference.

The present invention relates to a method of forming ester polyol esters (EPE) from ozone acids.

Figure 3:
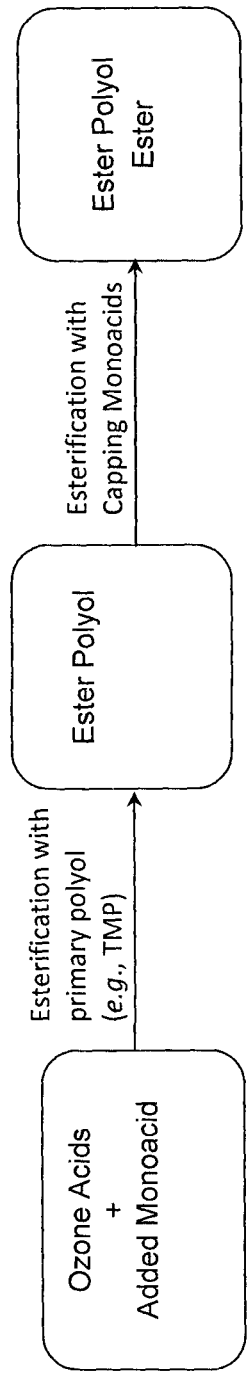
FIG. 3 shows the two-step conversion of ozone acids to lubricant base oil composed of the ester polyol esters of the present invention.

According to one aspect, there is provided a two-step process comprising a first step of esterifying ozone acids with at least one primary polyol to produce ester polyols (EP). The ester polyol is then further esterified with carboxylic acid to produce the ester polyol ester (EPE). FIG. 3 shows the two-step conversion of ozone acids to lubricant base oil composed of the ester polyol esters of the present invention.

The ester polyol according to the invention comprises the structure

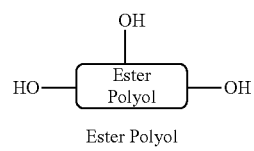

Ester Polyol

The ester polyol ester according to any aspect of the invention comprises the structure:

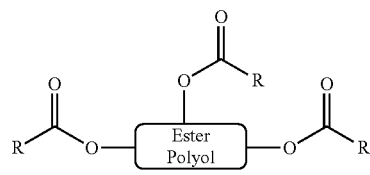

Figure 9:
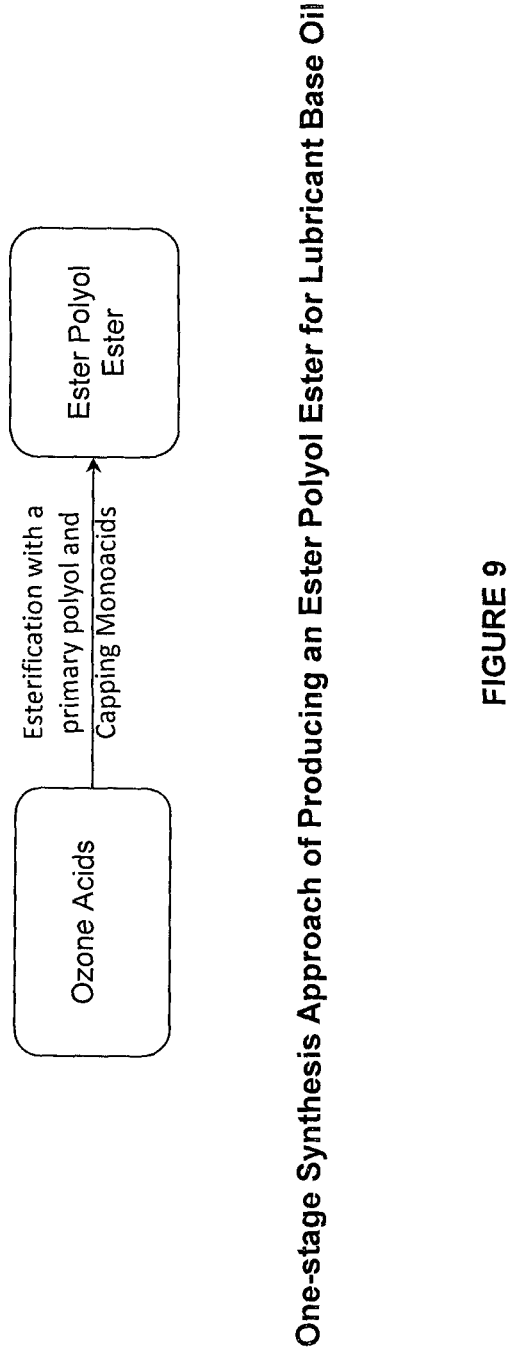
FIG. 9 is a simplified block diagram illustrating the one-step synthesis method of producing a ester polyol ester(s) for lubricant base oil.

According to another aspect, there is provided a one-step process comprising adding ozone acids, at least one primary polyol and optionally monoacids at the same time to form ester polyol esters (EPE). FIG. 9 is a simplified block diagram illustrating the one-step synthesis method of producing a ester polyol ester(s) according to the invention.

Accordingly, the present invention provides a method for preparing at least one ester polyol ester, the method comprising:

esterifying an ester polyol reaction mixture to produce ester polyol, the reaction mixture comprising an ozone acid mixture and at least one primary polyol, wherein the ozone acid mixture comprises at least one dicarboxylic acid and at least one monocarboxylic acid; and capping the ester polyol with at least one capping carboxylic acid to produce ester polyol ester.

In other words, the present invention provides a method for preparing at least one ester polyol ester, the method comprising:

esterifying at least one primary polyol with at least one dicarboxylic acid and at least one monocarboxylic acid to produce an ester polyol; and capping the ester polyol with at least one capping carboxylic acid to produce ester polyol ester.

When used in embodiments and aspects of the invention, the term "ozone acid mixture" refers to a mixture of the at least one dicarboxylic acid and at least one monocarboxylic acid.

When used in embodiments and aspects of the invention, the "polyol reaction mixture" refers to a mixture of the at least one primary polyol, the at least one dicarboxylic acid and at least one monocarboxylic acid.

When used in embodiments and aspects of the invention, the term "comprises" and variants thereof can be replaced by the term "consists" and variants thereof and vice versa.

In the method according to the invention,
(i) the ozone acid mixture may have a Difunctional/Monofunctional Ratio (DMR) corresponding to a ratio of moles of dicarboxylic acid to moles of monocarboxylic acid; and the ester polyol ester has a viscosity proportional to the DMR of the ozone acid mixture; and/or
(ii) the ester polyol reaction mixture may have a hydroxyl to carboxyl ratio (HCR) corresponding to a ratio of moles of —OH groups to moles of —COOH groups and the ester polyol ester has a viscosity inversely proportional to the HCR of the ester polyol, reaction mixture.

The ozone acid mixture according to any aspect of the invention may be prepared by reacting at least one fatty acid with ozone followed by oxidation. The oxidation may be with oxygen.

In any aspect of the invention, the ozone acid mixture may comprise at least one dicarboxylic acid and at least one first monocarboxylic acid; and the method may comprise adding at least one additional second monocarboxylic acid to the ozone acid mixture, wherein the first and second monocarboxylic acids may be different. The addition of the one or more additional second monocarboxylic acid may reduce the Difunctional/Monofunctional Ratio (DMR) of the ozone acid mixture.

In one particular aspect of the invention, the Difunctional/Monofunctional ratio (DMR) of the ozone acid mixture may be reduced from about 0.76 to about 0.05.

In one particular aspect of the invention, the ester polyol reaction mixture may comprise the at least one primary polyol in stoichiometric excess.

In one particular aspect of the invention, the ester polyol reaction mixture may have a hydroxyl to carboxyl ratio (HCR) corresponding to a ratio of moles of —OH groups to moles of —COOH groups and is from about 1.01 to about 2.0.

In one particular aspect of the invention, the ester polyol ester may have a viscosity proportional to the Difunctional/Monofunctional Ratio (DMR) of the ozone acid mixture, and the viscosity at 40° C. of the ester polyol ester may be from about 39.1 (cS) to about 236 (cS).

In one particular aspect of the invention, the at least one capping carboxylic acid may be one or more monocarboxylic acids. More in particular, the at least one capping carboxylic acid may be selected from the group consisting of: acetic, propanoic, butyric, pentanoic, hexanoic, nonanoic, 2-ethyl hexanoic, heptanoic, octanoic acid, decanoic, lauric, myristic, palmitic and stearic acids, and mixtures thereof. More in particular, the at least one capping carboxylic acid may be nonanoic acid.

In one particular aspect of the invention, the ester polyol ester may have a pour point from about −11.0° C. to about −57.0° C.

In one particular aspect of the invention, the at least one fatty acid may be derived from fractionated palm fatty acid distillate (PFAD); the hydroxyl carboxyl ratio (HCR) of the ester polyol reaction mixture may be about 1.25; the Difunctional/Monofunctional Ratio (DMR) of the ozone acid mixture may be from about 0.11 to about 0.21; the viscosity at 40° C. of the ester polyol ester may be from about 37.7 (cS) to about 61.6 (cS); and/or the ester polyol ester may have a pour point from about −57.0° C. to about −42.0° C.

In one particular aspect of the invention, the at least one fatty acid may be derived from palm kernel fatty acid distillate (PFKAD); the Difunctional/Monofunctional ratio (DMR) of the ozone acid mixture may be about 0.12; the hydroxyl carboxyl ratio (HCR) of the ester polyol reaction mixture may be about 1.25; and/or the viscosity at 40° C. of the ester polyol ester may be about 53.7 (cS).

In one particular aspect of the invention, the at least one fatty acid may be derived from a mixture of fractionated palm fatty acid distillate (PFAD) and palm kernel fatty acid distillate (PFKAD); the Difunctional/Monofunctional ratio (DMR) of the ozone acid mixture may be from about 0.05 to about 0.32; the hydroxyl carboxyl ratio (HCR) of the ester polyol reaction mixture may be about 1.25; and/or the viscosity of the ester polyol ester may be about 28 (CS) to about 120 (cS).

In one particular aspect of the invention, the at least one fatty acid may be derived from fractionated vegetable oleic acid; the Difunctional/Monofunctional ratio (DMR) of the ozone acid mixture may be from about 0.13 to about 0.3; the hydroxyl carboxyl ratio (HCR) of the ester polyol reaction mixture may be about 1.25; and/or the viscosity of the ester polyol ester may be about 37.92 (cS) to about 96.13 (cS).

The primary polyol according to any aspect of the invention may be selected from glycerin, diglycerin, ethylene glycol, diethylene glycol, 1,2-propanediol, bis(1,2-propanediol), 2-methyl-1,3-propanediol (2-MePG), trimethylolpropane (TMP), di-trimethylolpropane (Di-TMP), neopentyl glycol (NPG), pentaerythritol (PE), dipentaerythritol (diPE) and sorbitol. More in particular, the primary polyol may be a branched polyhydric primary polyol. More in particular, the primary polyol may be trimethylolpropane (TMP).

In one particular aspect of the invention, the ester polyol ester viscosity may be proportional to the Difunctional/Monofunctional Ratio (DMR) of the ozone acid mixture.

In one particular aspect of the invention, a lubricant base stock may be formed from the ester polyol ester; the lubricant base stock having a volatility that may be inversely proportional to the Difunctional/Monofunctional Ratio (DMR) of the ozone acid mixture.

In one particular aspect of the invention, the method may further comprise increasing the Difunctional/Monofunctional ratio (DMR) of the ozone acid mixture, thereby decreasing the volatility of the lubricant base stock.

In one particular aspect of the invention, the method may further comprise increasing the Difunctional/Monofunctional ratio (DMR) of the ozone acid mixture, thereby increasing the viscosity of the lubricant base stock.

In one particular aspect of the invention, the ester polyol ester may have a molecular weight (GPC) proportional to the Difunctional/Monofunctional Ratio (DMR) of the ozone acid mixture.

In one particular aspect of the invention, the method may further comprise increasing the hydroxyl/carboxyl ratio (HCR) of the ester polyol reaction mixture, thereby decreasing the viscosity of the lubricant base stock.

In one particular aspect of the invention, the one or more additional second monocarboxylic acids may be selected from the group consisting of: acetic, propanoic, butyric, pentanoic, hexanoic, nonanoic, 2-ethyl hexanoic, heptanoic, octanoic, decanoic, lauric, myristic, palmitic and stearic acids, and mixtures thereof. More in particular, the one or more additional second monocarboxylic acids may be selected from the group consisting of: hexanoic, nonanoic, 2-ethyl hexanoic, heptanoic, and octanoic acids.

The at least one fatty acid according to any aspect of the invention may be produced by hydrolyzing at least one triglyceride. In particular, the at least one triglyceride may comprise at least one vegetable oil and/or at least one animal fat. More in particular, the at least one vegetable oil may be selected from the group consisting of: soybean, safflower, linseed, corn, sunflower, olive, canola, sesame, cottonseed, mustard, camelina, jatropha, peanut, coconut, rapeseed, Chinese tallow, tung, castor, algae, wheat germ, soya, hemp, palm and palm kernel oils, palm olein, and a mixture thereof. More in particular, the at least one vegetable oil may comprise palm oil. In one particular aspect of the invention, the at least one vegetable oil may comprise palm olein. In one particular aspect of the invention, the at least one vegetable oil may comprise palm kernel oil. In one particular aspect of the invention, the at least one fatty acid may be derived from fractionated palm fatty acid distillate (PFAD). In one particular aspect of the invention, the at least one fatty acid may be derived from fractionated palm olein. In one particular aspect of the invention, the at least one fatty acid may be derived from palm kernel fatty acid distillate (PFKAD). In one particular aspect of the invention, the at least one animal fat may be selected from the group consisting of: fish oil, tallow, duck fat, and a mixture thereof.

In one particular aspect of the invention, a range of fatty acids and primary polyols may be used while maintaining a desired viscosity of the ester polyol ester, by increasing both the Difunctional/Monofunctional ratio (DMR) of the ozone acid mixture and the hydroxyl/carboxyl ratio (HCR) of the ester polyol reaction mixture.

In one particular aspect of the invention, the capping step may comprise using less than a stoichiometric amount of the at least one capping carboxylic acid. In particular, the amount of the at least one capping carboxylic acid used may be sufficient to achieve between about 62% to about 100% capping of the ester polyol. More in particular, the at least one capping carboxylic acid used is sufficient to achieve between about 62% to about 76% capping of the ester polyol. Yet further in particular, the ester polyol may be partially capped to produce a partially capped ester polyol ester which is between about 62% to about 99% capped. More in particular, the ester polyol may be partially capped to produce a partially capped ester polyol ester which is between about 62% to about 76% capped.

In one particular aspect of the invention, the partially capped ester polyol ester may have greater hydrolytic stability compared to an equivalent fully capped ester polyol ester.

In one particular aspect of the invention, the partially capped ester polyol ester may have greater viscosity compared to an equivalent fully capped ester polyol ester, while maintaining a similar pour point.

In one aspect of the invention, there is provided a method for preparing an ester polyol ester, the method comprising esterifying an ozone acid mixture comprising at least one monocarboxylic acid and at least one dicarboxylic acid, in the presence of at least one primary polyol. The ozone acid mixture may comprise at least one dicarboxylic acid and at least one first monocarboxylic acid; and the method may comprise adding at least one additional second monocarboxylic acid to the ozone acid mixture, wherein the first and second monocarboxylic acids may be different. The total amount of monocarboxylic acid may be sufficient to achieve a substantially capped ester polyol ester. The at least one monocarboxylic acid and the at least one additional second monocarboxylic acid may be substantially completely esterified. The total amount of the at least one primary polyol may be in stoichiometric excess. The total amount of hydroxyl functionality in the at least one primary polyol may be in stoichiometric excess of between 1% to 38%. The primary polyol may be selected from glycerin, diglycerin, ethylene glycol, diethylene glycol, 1,2-propanediol, bis(1,2-propanediol), 2-methyl-1,3-propanediol (2-MePG), trimethylolpropane (TMP), di-trimethylolpropane (Di-TMP), neopentyl glycol (NPG), pentaerythritol (PE), dipentaerythritol (diPE) and sorbitol. The ester polyol ester may have a pour point of from about −36° C. to about −51° C.

In particular, the method of the present invention preferably utilizes ozone acids produced from an oxidative ozonolysis process. More in particular, fatty acids, preferably derived from vegetable oil and/or animal oils, are initially subjected to oxidative cleavage so that all double bonds are cleaved and converted to carboxylic acid groups. In the oxidative cleavage of unsaturated fatty acids derived from vegetable oil or animal oils, a mixture of a diacid (azelaic acid) and monoacids (the mixture referred to as ozone acids) is produced.

According to one aspect of the present invention one or more fatty acids, for example a plurality or mixture of fatty acids, may be reacted with ozone to produce a mixture of ozone acids. The obtained ozone acids or mixture of ozone acids may comprise diacid and monoacid compounds. In particular, the (mixture of) ozone acids may have a Difunctional/Monofunctional Ratio (DMR) corresponding to a ratio of moles of diacid to moles of monoacid. The ozone acids are then esterified with primary polyols, such as but not limited to, neopentyl glycol (NPG), trimethylolpropane (TMP), pentaerythritol (PE), ditrimethylolpropane, dipentaerythritol, and the like. to form ester polyols. The resultant ester polyols are then esterified with at least one carboxylic acid to generate a unique class of ester polyol esters suitable for use as lubricant base stock.

Figure 4:
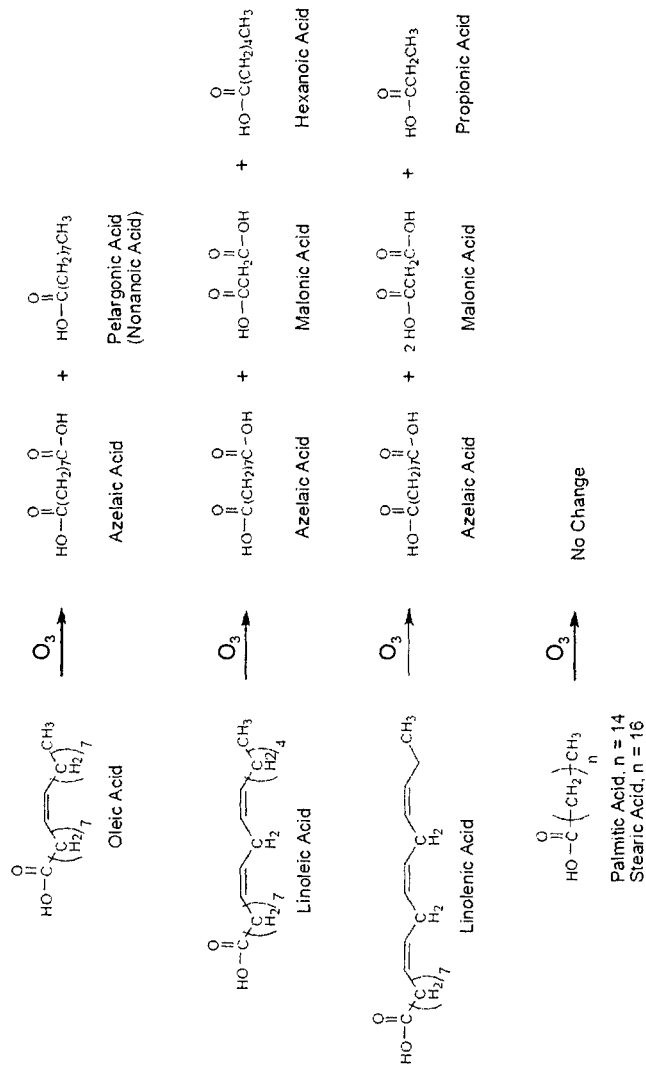
FIG. 4 illustrates the specific ozone acids formed by the oxidative ozonolysis of different fatty acids.

FIG. 4 illustrates the oxidative cleavage of representative fatty acids to produce specific mixtures of ozone acids. In this Figure, oleic acid is converted to azelaic acid and pelargonic acid (nonanoic acid); linoleic acid is converted to azelaic, hexanoic and acetic acids, and linolenic acid is converted to azelaic, acetic and propanoic acids. Acetic acid is formed from the decarboxylation of malonic acid under the combined oxidative ozonolysis reaction conditions. The saturated fatty acids such as palmitic and stearic acids remain unchanged.

Triglycerides such as palm oil, palm fatty acid distillates (PFAD), and palm kernel fatty acid distillates (PKFAD) or their alkyl esters can be hydrolyzed to produce fatty acids which serve as feedstocks for oxidative ozonolysis.

Examples of triglycerides include vegetable oil and animal fat. In particular, the triglyceride may be selected from palm oil, olein, soybean oil, safflower oil, linseed oil, corn oil, sunflower oil, olive oil, canola oil, sesame oil, cottonseed oil, mustard oil, camelina oil, jatropha oil, peanut oil, coconut oil, rapeseed oil, Chinese tallow oil, tung oil, castor oil, algae oil, wheat germ oil, soya oil, hemp oil, fish oil, tallow, duck fat, or the like, and a mixture thereof.

Sources of fatty acids include palm fatty acid distillate, fractionated palm fatty acid distillate, palm kernel fatty acid distillate, fractionated palm kernel fatty acid distillate, phospholipids, soybean oil fatty acid esters, palm oil fatty acid esters, phospholipids, or the like, or a mixture, or a fraction thereof.

Figure 1:
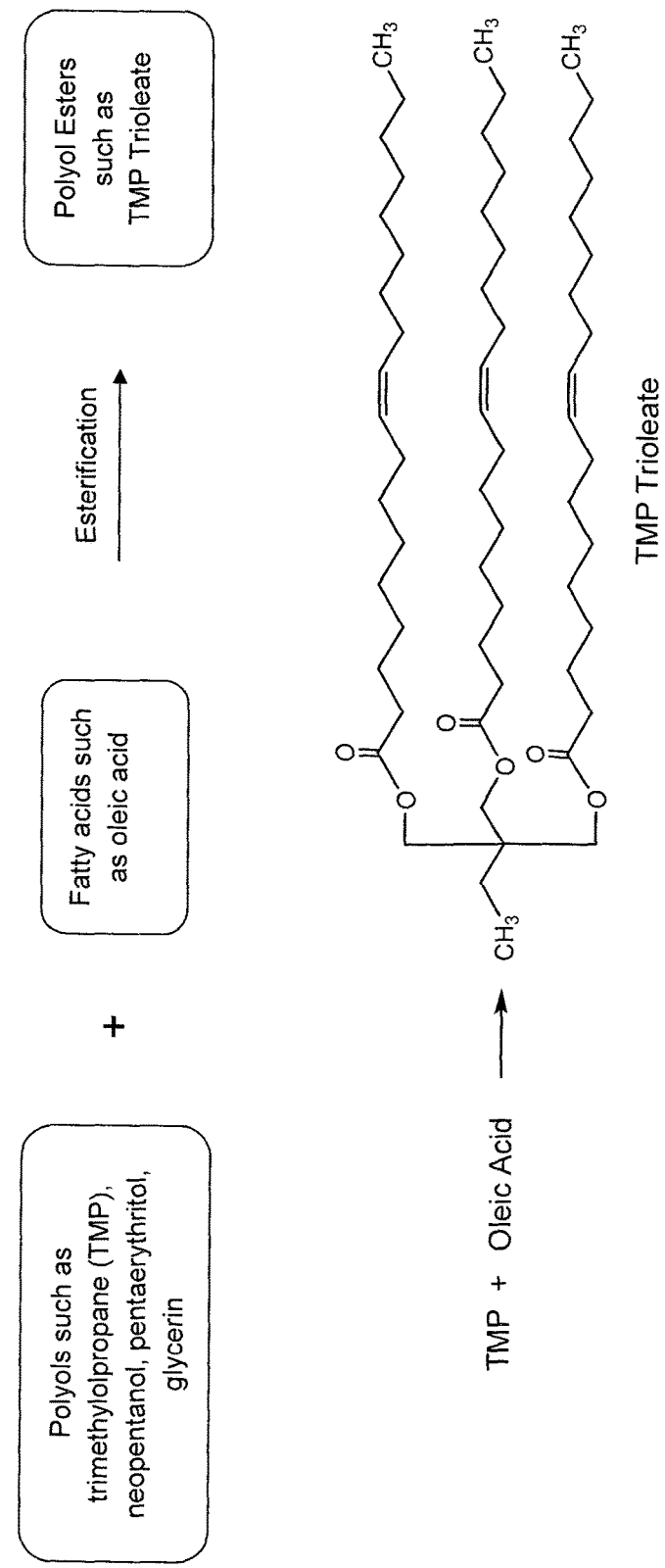
FIG. 1 shows the esterification of fatty acids such as oleic acid with polyols such as trimethylolpropane (TMP) to produce conventional polyol esters (PE) such as TMP trioleate.
Figure 2:
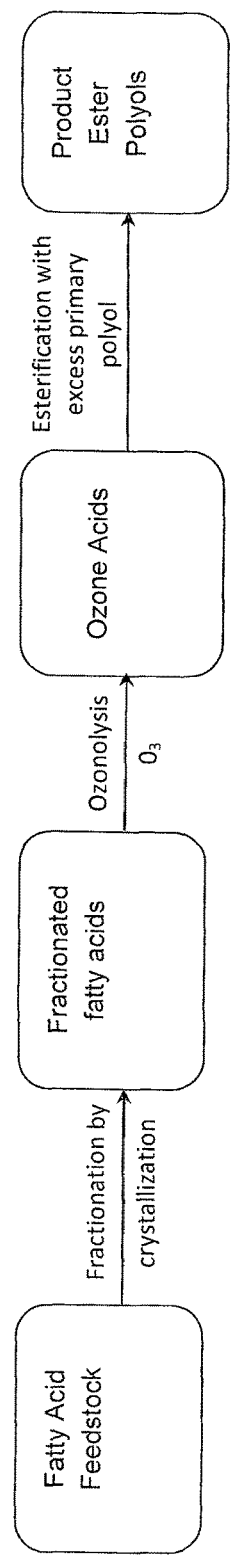
FIG. 2 is a simplified block diagram illustrating the conventional process of producing a mixture of ozone acids by ozonolysis of fractionated fatty acids and their esterification with excess primary polyol to form intermediate ester polyols (EP). The fatty acid feedstock in the simplified block diagram of FIG. 2 may be composed of vegetable oils, animal fats, fatty acids, and/or fatty acid esters optionally fractionated to reduce the saturated fatty acid content in the fractionated fatty acids. The fractionated fatty acids undergo a solvent-based oxidative ozonolysis reaction to produce ozone acids. The ozone acids are then esterified with excess primary polyol, e.g., glycerin to produce the product ester polyols.

FIG. 2 shows a simplified block diagram illustrating the conventional process of producing ester polyols via ozonolysis of fractionated fatty acids to form a mixture of ozone acids. The fatty acids are formed from the hydrolysis of triglyceride or fatty acid ester feedstock. The second-step of the conventional process is esterification of the ozone acids with excess primary polyol, typically TMP or glycerin, to form product ester polyols.

In FIG. 3, according to one aspect of the invention, mixtures of ozone acids and optional monofunctional carboxylic acids (monoacids) are esterified with primary polyols such as TMP to form ester polyols. By "primary polyol" we mean a polyol having two or more hydroxyl groups which can be used as a reactant in various processes. For example, the primary polyol can be used as a reactant in an ozonolysis process that uses at least one of its hydroxyl groups in forming ester linkages to fatty acid components in generating the secondary polyol, or as a reactant in an esterification process of an oxidation acid. The primary polyol may include glycerin, diglycerin, ethylene glycol, diethylene glycol, 1,2-propanediol, bis(1,2-propanediol), 2-methyl-1,3-propanediol (2-MePG); trimethylolpropane (TMP); di-trimethylolpropane (Di-TMP); neopentyl glycol (NPG); pentaerythritol (PE); dipentaerythritol (diPE); and sorbitol.

According to one aspect of the invention, the ester polyols are then esterified or capped with carboxylic acid to produce the ester polyol ester as part of the two-step conversion of the present invention, as shown in FIG. 3. Ester polyol esters in the present invention can be used widely for lubricant base stocks.

Examples of optional additional monoacids (used during first stage esterification) and capping monoacids include acetic, propanoic, butyric, pentanoic, hexanoic, heptanoic, octanoic, 2-ethylhexanoic, nonanoic, decanoic, lauric, myristic, palmitic and stearic acids and mixtures, thereof.

The one-step conversion of ozone acids to an ester polyol ester also uses these same monoacids.

According to one aspect of the invention, the ester polyols and ester polyol esters of the present invention may incorporate branched primary polyols. The branched primary polyols are effective in inhibiting phase separation in hydrocarbon chains, particularly from palm feedstock because palm feedstock contains high amounts of saturated fatty acids that cause phase separation. An example of a branched primary polyol is Trimethylolpropane (TMP) that is shown below.

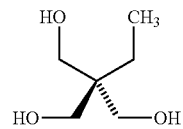

Branched primary polyols may be selected from 1,2-propanediol; 2-methyl-1,3-propanediol (2-MePG); trimethylolpropane (TMP); di-trimethylolpropane (Di-TMP); or neopentyl glycol (NPG). Following the esterification of the ozone acids, the product ester polyols are esterified with carboxylic acid to produce ester polyol esters.

In particular, the ester may have a repeated group ($RCO_2R'$) where R represents palmitate, stearate, hexanoate, nonanoate (pelargonate), propionate and azelate (as diesters) derived from the ozone acids. R' is derived from primary polyols.

Accordingly, in an embodiment, the ester polyol esters may be linear structures. In another embodiment, the ester polyol esters may be branched structures. Both may incorporate a branched primary polyols. The structure of the ester branched polyol esters hinders the close packing of hydrocarbon chains, which inhibits crystallization.

According to a particular aspect of the invention, the approach used to prepare ester polyol esters according to the invention that may used as lubricant base stock involves initial preparation of intermediate ester polyols by esterification of a mixture of ozone acids (mixtures of difunctional azelaic acid and monoacids) in the presence of a primary polyol, preferably in excess, plus additional monoacids as needed. The amount of primary polyols is characterized by their hydroxyl/carboxyl ratio (HCR) where the HCR is a ratio of moles of hydroxyl groups to moles of carboxyl groups.

Likewise, the ratio of azelaic acid to monoacids establishes the difunctional/monofunctional ratio (DMR) of ozone acids used to prepare each ester polyol. Intermediate ester polyols are then esterified or capped with excess monoacids in a second reaction so that almost all or all hydroxyl groups are converted to ester groups to form ester polyol esters. Both esterification reactions may be catalyzed by tin oxalate or tin oxide catalyst. This method is referred to as the two-step approach since two separate esterification reactions are employed, as shown in FIG. 3. In an industrial setting, both reactions would preferably be performed in the same vessel and the second step would be performed immediately after the first step without cooling the reaction mixture to avoid unnecessary heat loss.

In an aspect of the present invention, lubricant compositions are prepared from "synthetic" ozone acid mixtures expected to be produced from oxidative ozonolysis of a range of fatty acid-containing feedstocks. It is known that oxidative ozonolysis of fatty acids as specified by U.S. Pat. No. 2,813,113 and related patents results in generation of carboxylic acid functionality at each of the two carbon atoms that originally comprise the double bonds of each fatty acid before undergoing oxidative cleavage. Examples of individual ozone acids produced from the oxidative ozonolysis of select individual fatty acids are illustrated in FIG. 3. This knowledge allows one to calculate and predict the specific percentages of the diacid azelaic acid and all monoacids resulting from oxidative ozonolysis of any fatty acid feedstock composition. Accordingly, all lubricant compositions described herein were prepared from specific diacid and monoacids expected to be produced from oxidative ozonolysis of a range of fatty acid-containing feedstocks. Different ozone acid compositions were prepared by mixing together the calculated amounts of diacid (e.g., azelaic acid) and monoacids using purchased high-purity compounds. We refer to these "synthetic" ozone acid mixtures as simulated ozone acids. Two specific sets of simulated ozone acids were extensively used in the development and these were derived from PFAD and Edenor OL-72. (a) PFAD represents the ozone acids expected from palm oil fatty acid distillate (12% palmitic acid, 1.5% myristic acid, 68% oleic acid, and 16% linoleic acid) which results in a DMR of 0.71 (b) Edenor OL-72 represents an ozone acid mixture expected from olein that had been purified to contain nominally 72 percent oleic acid and the specific composition that was simulated contained 75.6% oleic acid, 11.4% linoleic acid, 4.41% palmitic, 2.8% stearic acid and 4.5% myristic acid which resulted in ozone acids with a DMR of 0.762.

An advantage of this approach is that we were able to prepare specific ozone acid compositions predicted to result from any fatty acid feedstock available worldwide. On the other hand, only one ozone acid composition is commercially available and that composition results from the oxidative ozonolysis of a specific fatty acid mixture obtained from purified tallow.

One specific simulated ozone acid mixture used to prepare the ester polyols was the mixture predicted to be obtained from the oxidative ozonolysis of palm based fatty acid. The compositions of the simulated ozone acid mixtures derived from PFAD, fractionated PFAD, palm kernel fatty acid distillate (PKFAD), and the ozone acid mixture derived from partially purified olein such as Edenor OL-72 (produced by Emery Oleochemicals) were predicted knowing the specific fatty acid composition of each feedstock. Edenor OL-72 is a fatty acid mixture containing about 72% oleic acid content. Any suitable fatty acid mixture having a high oleic content may be used as the feedstock for ozone acids. Preferably, an ozone acid mixture with a high percentage of oleic acid is used because it results in a lower percentage of saturated fatty acids.

The lubricant base stock of the present invention has improved physical properties, such as, viscosity, pour point, and molecular weight. The ability to correlate changes to the polyol structure with differences in the performance properties is a feature of the present invention. There are several compositional factors, such as the amount and identity of ozonolysis feedstock, primary polyols, extra added monoacids, and capping monoacids that influence the properties of lubricant base oil. The specific combination of these compositional factors establishes key parameters known as the carboxylic acid difunctional to monofunctional ratio (DMR) and the hydroxyl to carboxyl ratio (HCR), which dictate the structure of intermediate ester polyols. By definition, the intermediate ester polyols will require hydroxyl to carboxyl ratios of greater than 1.0 in the polyol(s) and acid(s) used to make said intermediate.

These selective ratios are critical factors in providing unique characteristics in terms of superior performance in low temperature fluidity, thermal stability, and broader viscosity profiles of lubricant base stocks. The difunctional to monofunctional ratio (DMR) of the ozone acids is critical in achieving the desired polyol ester molecular weights, which results in achieving the targeted ester polyol ester viscosity and volatility after capping reactions. The viscosity, volatility, and molecular weight of the ester polyol esters are also found to be dependent on the DMR of the ozone acids and any extra monofunctional acids that may be added in preparing the intermediate ester polyols. This proves to be vital in terms of the usage of the ester polyol esters for high performance lubricant applications.

The present invention will also show that modifying the hydroxyl to carboxyl ratio (HCR) has an effect towards adjusting the ester polyol ester viscosity.

An object of the present invention is to demonstrate variations in viscosities, pour points, and/or volatilities of the ester polyol esters and dependence of these properties on the compositional properties of the ester polyols from which they are derived. A major factor that influences the ester polyol and ester polyol ester viscosities is the DMR of the ozone acid mixtures used to prepare the ester polyols. The DMR is the ratio of the molar amount of diacid to monoacids in the ozone acid or ozone acid mixtures that can also include added monoacids as needed. The use of higher DMR feedstocks results in increased ester polyol and ester polyol ester viscosities and decreased volatilities. Conversely, a decreased DMR feedstock results in decreased ester polyol component molecular weights, resulting in decreased viscosities and increased volatilities of the ester polyols and ester polyol esters.

Figure 5:
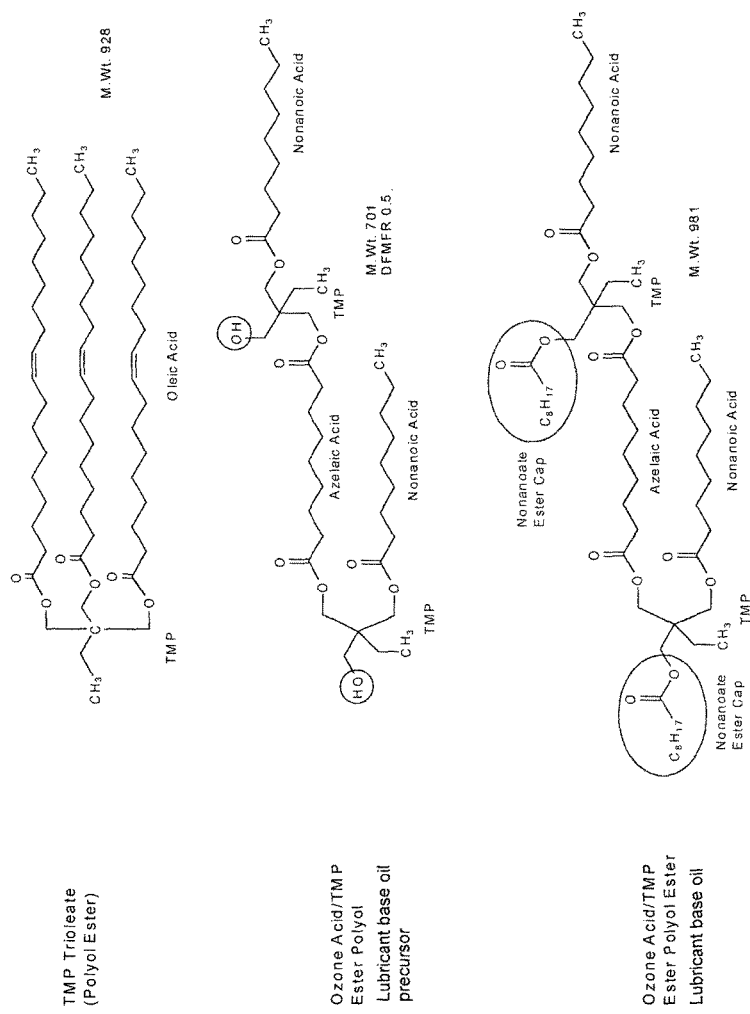
FIG. 5 illustrates the structures of the polyol ester TMP trioleate, an intermediate ester polyol lubricant base oil precursor, and an ester polyol ester lubricant base oil.

FIG. 5 shows structures of the polyol ester TMP trioleate (top), lubricant ester polyol base oil precursor formed by the esterification reaction of select ozone acids with TMP (middle), and ester polyol ester formed by the esterification reaction of ester polyol lubricant base oil precursor (bottom). The middle structure in FIG. 5 is the lubricant base oil precursor formed after the first-step of the two-step conversion of the ozone acid with the primary polyol TMP in the present invention. The bottom structure in FIG. 5 is the lubricant base oil or ester polyol ester of the present invention formed after the ester polyol is esterified with capping monoacids. In this example, the hydroxyl groups of the ester polyol are esterified by nonanoic acid, also named pelargonic acid. Nonanoic acid is a typical capping monoacid used during the second-step of esterification of the ester polyol. The final structure is an ester polyol ester, which is used as a lubricant base oil.

The DMR is a key parameter in controlling lubricant basestock viscosity and volatility. Since the only difunctional acid resulting from oxidative ozonolysis of unsaturated fatty acids is azelaic acid, it can be seen that DMR ratios will be higher the higher the feedstock unsaturation level and lower the lower the feedstock unsaturation level. Based on the composition of fractionated PFAD, the DMR of the ozone acid composition resulting from oxidative ozonolysis of fractionated PFAD is 0.71. By comparison, the DMR of the ozone acids resulting from oxidative ozonolysis of soybean oil fatty acids has a value of 1.51 due to the increased level of unsaturation in soybean oil. The DMR of any ozone acid composition may be adjusted downward as necessary by the addition of monoacids to access compositional ranges of a polyol which suits the lubricant base stock. In general, increased DMR values indicate increased amounts of azelaic acid that favors the formation of higher molecular weight structures and more crosslinked structures in the presence of trifunctional or higher functionality primary polyols. These molecular effects result in higher viscosities and lower volatilities.

In the ester polyols, increased amounts of primary polyol hydroxyl functionality relative to available carboxyl functionality results in increased HCR values and increased hydroxyl functionality after esterification. Thus, the higher the amount of primary polyol relative to carboxyl functionality as measured by increased HCR, the higher the resulting hydroxyl value (HV) of intermediate ester polyols. The viscosities of resulting ester polyols and ester polyol esters are also expected to increase as the HCR is reduced. This is because a reduction in HCR leads to increased incorporation of the primary polyol hydroxyl groups leading to increased molecular weights if the primary polyol has two hydroxyl groups and increased crosslinking if the primary polyol has three or more hydroxyl groups. Thus, control of the feedstock DMR, which is characteristic of different ozone acid feedstocks and which can be readily reduced by addition of external monoacids, and HCR as well as choice of primary polyols can be used to produce a wide range of ester polyol esters lubricant base stocks having varying structure, viscosities, and volatilities.

The esterification of appropriate palm-based ester polyols with monoacids produced lubricant base oil with appropriate ranges of viscosities, pour points, and volatilization properties. Without such ester polyol esterification, critical performance properties would not be achieved for most lubricant applications.

When using TMP as the primary polyol, the ISO viscosities, which are viscosities measured in centistokes (abbreviated cS) at 40° C. of ester polyol esters were strongly dependent on the DMR of the ozone acid feedstock used to prepare intermediate ester polyols. This feature is understandable on a molecular basis since higher amounts of difunctional acids will give rise to increased crosslinking between TMP (which contains three hydroxyl groups per molecule) resulting in higher lubricant base oil viscosities. Conversely, increased amounts of monofunctional acids, which results in lower DMR will block the relative ability of TMP to undergo crosslinking involving TMP due to blocking one or more of TMP hydroxyl groups with monoacid esters, leading to decreased viscosities.

When using TMP as the primary polyol, lubricant base stock viscosities were inversely dependent on the hydroxyl to carboxyl ratios (HCR) used to prepare intermediate ester polyols. This is because when the polyol is reacting with a mixture of diacids and monoacids, the greater the excess of TMP hydroxyl groups compared to total acid groups, the lower the percentage of TMP that will undergo crosslinking with diacids (which requires incorporations of all three of TMP's hydroxyl groups). Diminishing crosslinking will reduce ester polyol and derived lubricant base oil viscosities. Conversely, if one allows the HCR to be reduced to near 1 (nearly equal amounts of TMP hydroxyl groups and ozone acid carboxylic groups) when reacting with the same mixture of diacids and monoacids, there will be a greater percent involvement of TMP's three hydroxyl groups, which will lead to higher crosslinking and increased viscosities.

According to one aspect, the present invention provides an ester polyol ester obtained or obtainable by the above methods According to one aspect, the present invention provides an ester polyol ester lubricant base oil comprising the ester polyol ester obtained or obtainable by the above methods According to one aspect, the present invention provides an ester polyol ester lubricant base oil comprising the reaction product of at least one carboxylic acid and at least one ester polyol, wherein the ester polyol may have at least one ester group, a first hydroxyl group, and at least a second hydroxyl group. The ester polyol ester lubricant base oil may have a molecular weight (GPC) of about 700-1900 g/mol. The at least one carboxylic acid may be selected from the group consisting of: acetic, propanoic, butyric, pentanoic, hexanoic, nonanoic, 2-ethyl hexanoic, heptanoic, octanoic, decanoic, lauric, myristic, palmitic and stearic acids, and mixtures thereof. In particular, the at least one carboxylic acid may be nonanoic acid. The ester polyol ester lubricant base oil may have a pour point of below about −11.0° C. In particular, the ester polyol ester lubricant base oil may have a pour point of between about −57.0° C. to about −11.0° C.

According to one aspect, the present invention provides an ester polyol ester composition comprising a compound of Formula I:

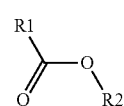

Formula I wherein R1 is a linear or branched alkyl chain having from 1 to 17 carbon atoms, optionally substituted with one or more hydroxyl groups, or R1 is a linear alkyl chain with from 2 to 18 carbon atoms and a terminal carboxylic acid group which isoptionally esterified with a polyol compound of formula R2-OH;

R2, when attached to a hydroxyl group, is a linear or branched primary polyol having from 2 to 12 carbon atoms, wherein each alcohol functional group is optionally esterified with a monocarboxylic acid or dicarboxylic acid of formula R1-COOH, or a monocarboxylic acid of formula R3-COOH; and R3 is a linear or branched alkyl chain having from 1 to 17 carbon atoms, optionally substituted with one or more hydroxyl groups.

According to one aspect, the present invention provides an ester polyol ester composition comprising a compound of Formula II:

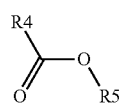

Formula II wherein R4 is the alkyl chain of a monocarboxylic acid selected from the group consisting of: acetic, propanoic, butyric, pentanoic, hexanoic, nonanoic, 2-ethyl hexanoic, heptanoic, octanoic acid, decanoic, lauric, myristic, palmitic and stearic acids, or R4 is a C2-C18 linear alkyl chain with a terminal carboxylic acid group which is optionally esterified with a polyol compound of formula R5-OH;

R5, when attached to a hydroxyl group, is the alkyl chain of a primary polyol selected from the group consisting of: glycerin, diglycerin, ethylene glycol, diethylene glycol, 1,2-propanediol, bis(1,2-propanediol), 2-methyl-1,3-propanediol (2-MePG), trimethylolpropane (TMP), di-trimethylolpropane (Di-TMP), neopentyl glycol (NPG), pentaerythritol (PE), dipentaerythritol (diPE) and sorbitol, wherein each alcohol functional group is optionally esterified with a monocarboxylic acid or dicarboxylic acid of formula R4-COOH, or a monocarboxylic acid of formula R6-COOH; and R6 is the alkyl chain of a monocarboxylic acid selected from the group consisting of: acetic, propanoic, butyric, pentanoic, hexanoic, nonanoic, 2-ethyl hexanoic, heptanoic, octanoic acid, decanoic, lauric, myristic, palmitic and stearic acids.

According to one aspect, the present invention provides an ester polyol ester composition comprising a compound of Formula III:

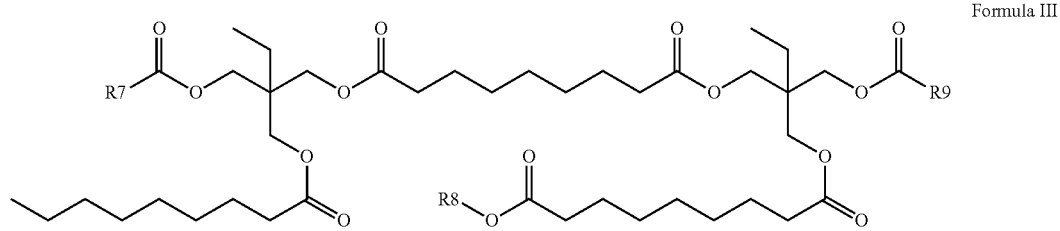

Formula III wherein R7, R8 and R9 are independently:
a linear or branched alkyl chain of between 1 to 17 carbon atoms, optionally substituted with one or more hydroxyl groups;
a C2-C18 linear alkyl chain with a terminal carboxylic acid group which is optionally esterified with a polyol compound of formula R10-OH; or
R10, wherein R10, when attached to a hydroxyl group, is a linear or branched primary polyol having from 2 to 12 carbon atoms and each alcohol functional group in R10 is optionally esterified with a linear or branched monocarboxylic acid having from 2 to 18 carbon atoms, or a dicarboxylic acid having from 3 to 9 carbon atoms.

According to one aspect, the present invention provides an ester polyol ester composition comprising a compound of Formula IV:

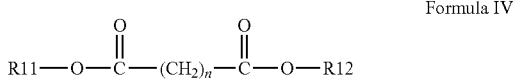

Formula IV wherein n is from 0 to 16;
R11 and R12, when each attached to a hydroxyl group, are independently a linear or branched primary polyol having from 2 to 12 carbon atoms, wherein each alcohol functional group is optionally esterified with a monocarboxylic acid of formula R13-COOH or dicarboxylic acid of formula R14-COOH;
R13 is a linear or branched alkyl chain having from 1 to 17 carbon atoms, optionally substituted with one or more hydroxyl groups; and
R14 is a C2-C18 linear alkyl chain with a terminal carboxylic acid group which is optionally esterified with a primary polyol compound of formula R11-OH or R12-OH.

According to one aspect, the present invention provides an ester polyol ester composition comprising an azelaic acid ester polyol ester wherein azelaic acid is esterified with at least one polyol of formula R15-OH; wherein each polyol R15-OH is a linear or branched primary polyol having from 2 to 12 carbon atoms and contains at least two alcohol functional groups which are independently optionally esterified with a carboxylic acid of formula R16-COOH; and R16 is chosen from the group consisting of: a linear or branched alkyl chain having from 1 to 17 carbon atoms, optionally substituted with one or more hydroxyl groups; and a C2-C18 linear alkyl chain with a terminal carboxylic acid group which is optionally esterified with a polyol compound of formula R15-OH.

Table A shows the progression of experiments that led to obtaining lubricant base oil candidates having viscosities in the ISO 44-46 cS viscosity range while simultaneously achieving very low pour points. Lubricants with ISO viscosities in the 44-46 cS have high general applicability as hydraulic fluids. In this study, simulated compositions of ozone acids expected to be formed from of PFAD (palm fatty acid distillate) and PKFAD (palm kernel fatty acid distillate) were esterified with TMP and the resulting polyols were capped with nonanoic acid. Crystallization onset temperatures (COT) were initially used to estimate pour points.

TABLE A

Ester Polyol Ester Lubricant Base Oil Trends Caused by Variations in DMR and HCR of Ester Polyols in Simulated Composition Ozone acids

| Exp. No. | Simulated Compositions of Ozone Acids[a] | DMR | HCR | Viscosity @ 40° C. (cS) | COT[b] or Pour Point (° C.) |
|---|---|---|---|---|---|
| 1 | PFAD | 0.71 | 1.11 | ~2690 | COT: −20 |
| 2 | PFAD[c] | 0.71 | 1.25 | ~720 | COT: −25 |
| 3 | PKFAD | 0.12 | 1.25 | 53.7 | COT: −13 Pour Pt.: −11 |
| 4 | PFAD + Nonanoic Acid | 0.21 | 1.24 | 61.6 | COT: −39 Pour Pt.: −42 |
| 5 | PFAD + Nonanoic Acid | 0.11 | 1.25 | 37.7 | COT: None Pour Pt.: −48 |
| 6 | PFAD + Nonanoic Acid | 0.134 | 1.25 | 44.2 | COT: −50 Pour Pt.: −57 |

[a]Esterified with TMP and capped with nonanoic acid
[b]COT: crystallization onset temperature determined by DSC
[c]Capped with mixture of $C_8$ and $C_9$ acids In Experiment No. 1, a much higher than desired ISO viscosity was obtained when the simulated composition of ozone acids derived from PFAD with an inherent DMR of 0.71 were used in combination with a relatively low HCR value of 1.11. In Experiment No. 2, the HCR was increased to 1.25 which led to a partial reduction in the ISO viscosity, as expected. In experiments 1 and 2, only crystallization onset temperatures (COTs) were measured and these can be taken to approximate the pour points of these mixtures since both COT and pour points were determined in other experiments in Table A and there is a fairly good agreement between these two measurements. In Experiment No. 3, the HCR was maintained but the DMR was reduced to 0.12 as a result of using a PKFAD simulated composition of ozone acids. This was caused by the significantly decreased concentration of oleic acid and increased amounts of monofunctional acids in PKFAD simulated ozone acids compared to PFAD simulated ozone acids). It can be seen these changes resulted in a further drop in ISO viscosity (53.7 cS) which is close to the desired range. This drop in ISO viscosity is primarily due to the appreciable drop in DMR from 0.71 to 0.12 (while keeping the HCR the same) in the initially formed ester polyol. The significantly increased pour point in Experiment 3 was due to the fact that simulated PKFAD ozone acids contain significantly greater amounts of high melting $C_{12}$, $C_{14}$ and $C_{16}$ saturated fatty acids than simulated PFAD ozone acids.

In sequential experiments 4, 5, and 6 listed in Table A, the simulated composition of ozone acids derived from PFAD was used while using variable amounts of monofunctional nonanoic acid to adjust DMR values while maintaining constant HCR values in initially formed ester polyols. Since the object of the experiments was to obtain an ester polyol ester ISO viscosity value in the 44-46 cS range, experimentation was stopped with experiment 6 when an ISO viscosity of 44.2 cSt was achieved along with a pour point of −57° C. The low pour point results from the incorporation of lower molecular weight nonanoic acid (a saturated fatty acid) in replacement of higher molecular weight saturated fatty acids. The combined performance properties are characteristic of a premium lubricant base oil.

Figure 6:
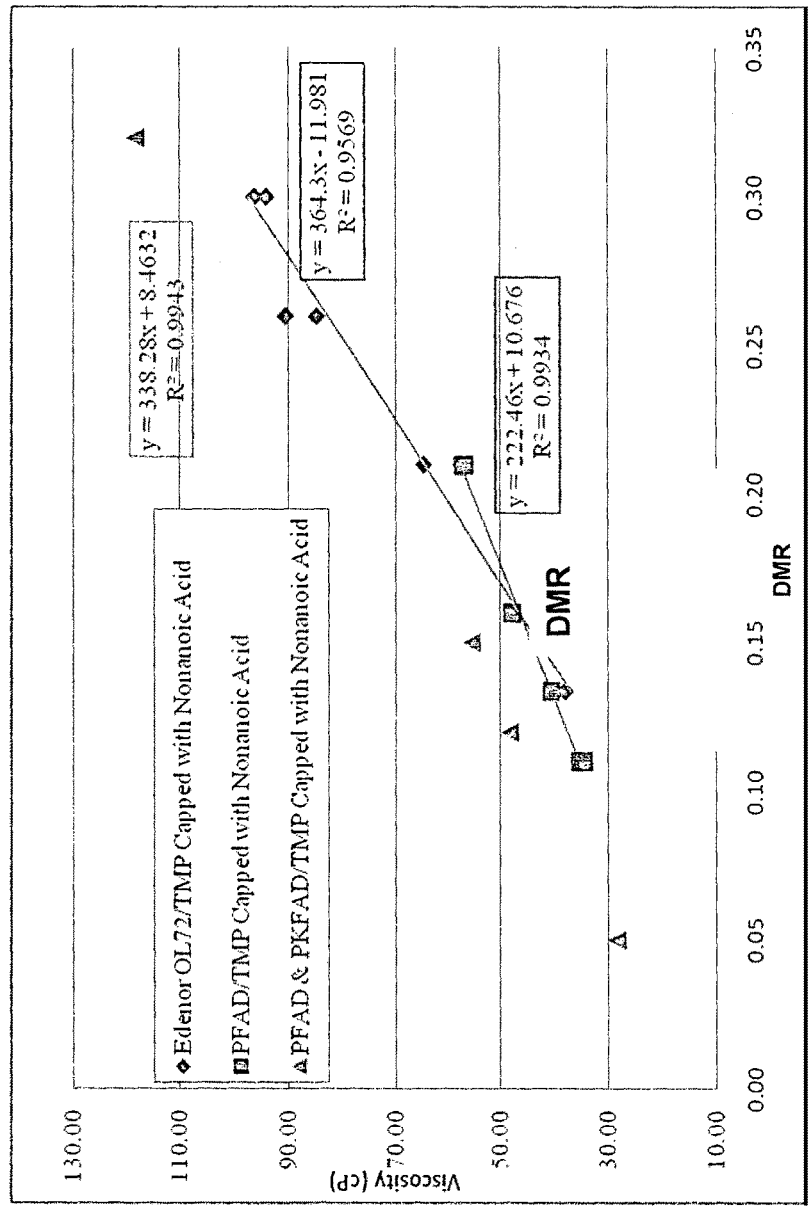
FIG. 6 is a graph of ester polyol ester viscosities versus the DMR of the ozone acids at a HCR of 1.25 after capping with Nonanoic Acid.

Data of the type shown in Table A is plotted in FIG. 6 where the viscosities (in centipoise or cP) of nonanoic acid-capped TMP-based ester polyols (ester polyol esters) are plotted against the DMR of precursor ester polyols while maintaining the HCR at 1.25. The ester polyols were prepared from the esterification of simulated ozone acids expected to be produced from fractionated oleic acid nominally containing 72 percent oleic acid (Edenor OL-72 produced by Emery Oleochemicals), PFAD and mixtures of PFAD and PKFAD while various amounts of nonanoic acid was added to achieve various DMR values. Each type of virtual ozone acid describes a separate line and it can be seen that plots of viscosities versus DMR are relatively linear. The relatively large slopes of these lines indicate that lubricant base oil viscosities are highly dependent on their DMR values. The viscosities of mixtures of PKFAD and PFAD ozone acids were greater than those of simulated high oleic acid and PFAD at any DMR value. This trend is attributed to the fact that PKFAD contains greater amounts of higher molecular weight saturated fatty acids than simulated high Oleic and PFAD by itself. Of importance is the fact that a range of viscosities ranging from about 40 cP to about 100 cP were obtained using a simulated composition of ozone acids corresponding to the composition of PFAD containing variable amounts of nonanoic acid and after capping the initially produced ester polyol with nonanoic acid. This behavior indicates that a wide range of lubricant base oil candidates can be obtained from this starting material by simply adjusting the DMR of the precursor ester polyols. Furthermore, it can be seen that plots such as those shown in FIG. 6 allow the operator to "dial in" desired viscosities by simply adjusting DMR values when operating at one HCR value.

TABLE B

Polyol ester Viscosity versus DMR at HCR of 1.25 After Capping with Nonanoic Acid

| LRB No. | Simulated Compositions of Ozone Acids[a] | DMR | HCR | Viscosity (cP) |
|---|---|---|---|---|
| 52921-25-29 | PFAD & PKFAD/TMP Capped with Nonanoic Acid | 0.05 | 1.25 | 28.31 |
| 52781-76-29 | PFAD & PKFAD/TMP Capped with Nonanoic Acid | 0.12 | 1.25 | 48.28 |
| 52921-20-29 | PFAD & PKFAD/TMP Capped with Nonanoic Acid | 0.15 | 1.25 | 55.46 |
| 52921-29-30 | PFAD & PKFAD/TMP Capped with Nonanoic Acid | 0.32 | 1.25 | 118.3 |
| 52921-111-31 | Edenor OL72/TMP Capped with Nonanoic Acid | 0.1336 | 1.25 | 37.92 |
| 52921-98-27 | Edenor OL72/TMP Capped with Nonanoic Acid | 0.21 | 1.25 | 64.71 |
| 53212-9-29 | Edenor OL72/TMP Capped with Nonanoic Acid | 0.26 | 1.25 | 84.68 |
| 52921-97-28 | Edenor OL72/TMP Capped with Nonanoic Acid | 0.26 | 1.25 | 90.37 |
| 52921-100-29 | Edenor OL72/TMP Capped with Nonanoic Acid | 0.3 | 1.25 | 93.97 |
| 53212-11-28 | Edenor OL72/TMP Capped with Nonanoic Acid | 0.3 | 1.25 | 96.13 |
| 52921-38-29 | PFAD/TMP Capped with Nonanoic Acid | 0.11 | 1.25 | 35.09 |
| 52921-51-29 | PFAD/TMP Capped with Nonanoic Acid | 0.1336 | 1.25 | 40.47 |
| 52921-47-28 | PFAD/TMP Capped with Nonanoic Acid | 0.16 | 1.25 | 47.83 |
| 52921-30-30 | PFAD/TMP Capped with Nonanoic Acid | 0.21 | 1.25 | 57.24 |

Figure 7:
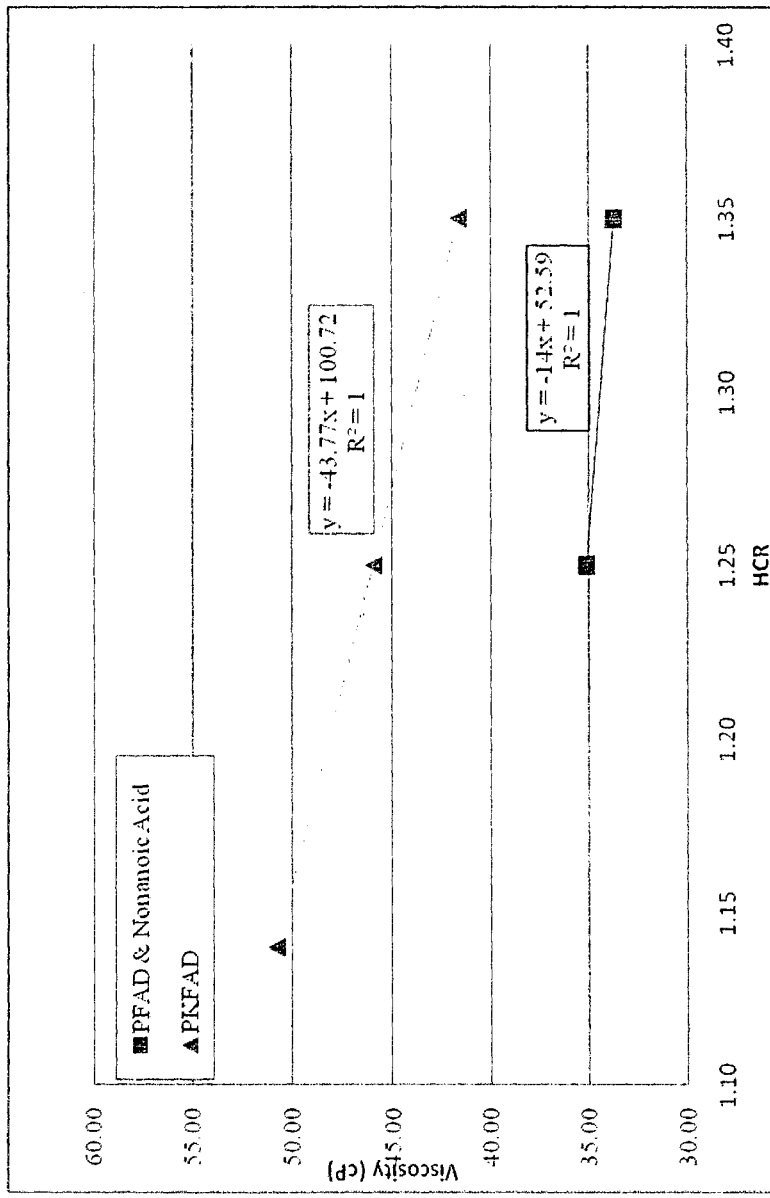
FIG. 7 is a graph of polyol ester viscosities versus the HCR (at DMR of 0.12) after capping with Nonanoic Acid.

Shown in FIG. 7 are plots of the viscosities of TMP-based lubricant base oil candidates versus HCR values of the ester polyols obtained when the DMR was maintained from 0.11 to 0.12. The lubricant base oil candidates were prepared from simulated compositions of ozone acids expected from PFAD or PKFAD while adding nonanoic acid to adjust the DMR to the stated value. It can be seen that the plots of viscosities versus HCR at constant DMR are relatively linear (based on the PKFAD plot) and the viscosities are inversely related to HCR. Also, the slopes of the lines in FIG. 7 are significantly less than those in FIG. 6, which indicates that DMR variations have a greater effect on viscosities than HCR variations. The viscosities of the PKFAD system were greater than those of the PFAD system at all HCR values and this trend is attributed to the fact that PKFAD contains greater amounts of higher molecular weight saturated fatty acids than PFAD. The values for the polyol ester viscosities versus DMR of about 0.12 after capping with Nonanoic acid are listed in Table C.

TABLE C

Polyol Ester Viscosities versus HCR at DMR of 0.12 After Capping with Nonanoic Acid

| LRB No. | | DMR | HCR | Viscosity (cP) |
|---|---|---|---|---|
| 52921-22-28 | PKFAD | 0.12 | 1.15 | 50.84 |
| 52921-2-32 | PKFAD | 0.12 | 1.25 | 45.97 |

TABLE C-continued

Polyol Ester Viscosities versus HCR at DMR
of 0.12 After Capping with Nonanoic Acid

| LRB No. | | DMR | HCR | Viscosity (cP) |
|---|---|---|---|---|
| 52921-19-31 | PKFAD | 0.12 | 1.35 | 41.65 |
| 52921-38-29 | PFAD & Nonanoic acid | 0.11 | 1.25 | 35.09 |
| 52921-40-29 | PFAD & Nonanoic acid | 0.11 | 1.35 | 33.69 |

Based on FIGS. 6 and 7, it can be seen that the viscosities of lubricant base oil candidates can be adjusted to desired values by adjusting either the DMR and HCR of the polyol used to prepare the final base oil when followed by capping with monoacids, such as, nonanoic acid. This allows producers to obtain a variety of base oil ISO viscosities by independent adjustment of the parameters or adjustment in concert with each other to obtain desired viscosities.

TABLE D

TMP-Based Lubricant Base Oil
Properties at Increased DMR and HCR

| Exp. No. | Simulated Ozone Acids[a] | DMR | HCR | Viscosity @ 40° C. (cS) | Pour Point (° C.) | Percent Simulated Composition of Ozone Acids |
|---|---|---|---|---|---|---|
| 1 | Edenor OL-72 + Non. Acid[b] | 0.134 | 1.25 | 56 | −54 | — |
| 2 | Edenor OL-72 + Non. Acid[b] | 0.40 | 2.0 | 49 | −54 | 23.0 |
| 3 | Edenor OL-72 + Non. Acid[b] | 0.60 | 2.0 | 69 | −54 | 28.8 |
| 4 | Edenor OL-72 + Non. Acid[b] | 0.60 | 2.3 | 58 | −51 | — |
| 5 | Edenor OL-72 | 0.76 | 1.7 | 130 | −42 | 38.6 |
| 6 | Edenor OL-72 | 0.76 | 1.8 | 96 | −42 | 36.2 |
| 7 | Edenor OL-72 | 0.76 | 1.10 | 76 | −51 | 34.1 |
| 8 | Emery Ozone Acids + Nonanoic Acid | 0.50 | 1.25 | 236 | −30 | — |

Figure 8:
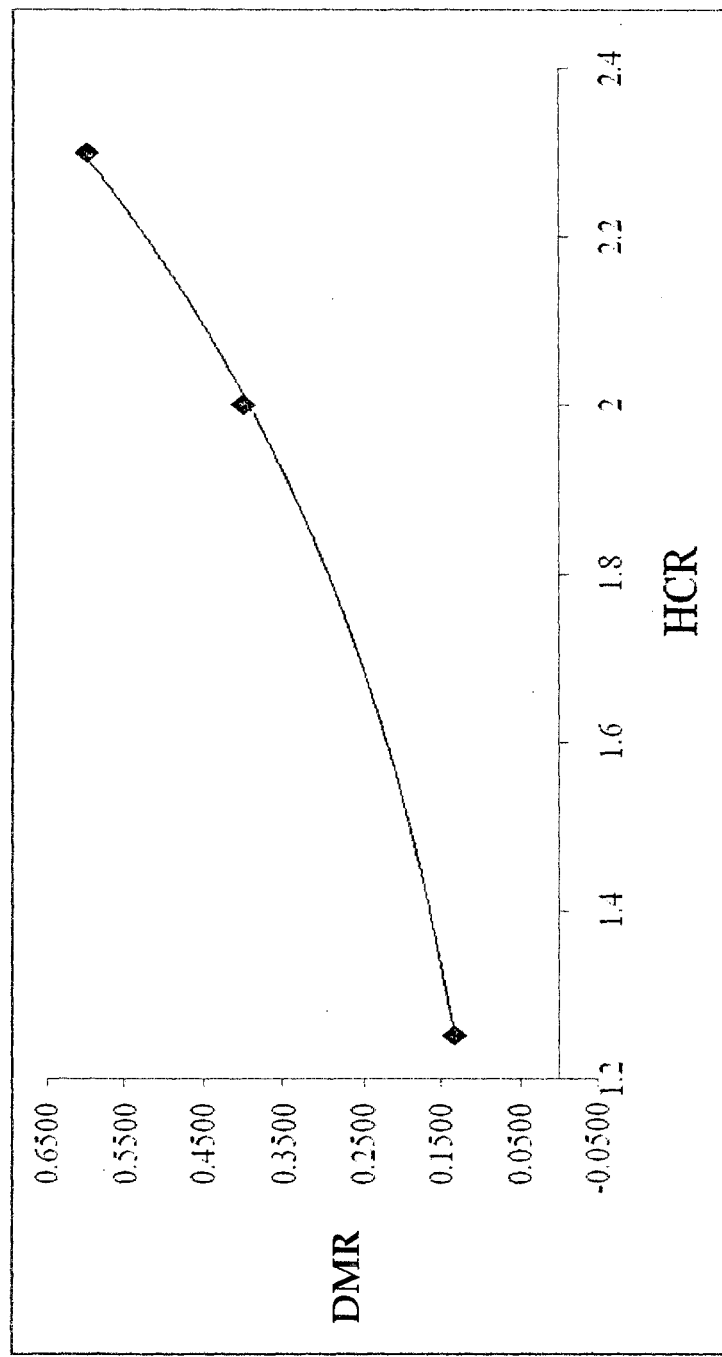
FIG. 8 is a graph of the combined DMR and HCR required to obtain ISO 49-58 cS lubricant base oil.

[a]Esterified with TMP and nonanoic acid (where shown) and capped with nonanoic acid
[b]Non. Acid: nonanoic acid Table D supports the trend that ISO viscosities of ester polyol ester lubricant base oils increase with increasing values of DMR and decrease with increasing values of HCR of the corresponding ester polyols. Combination of these two trends predicts that a plot of DMR versus HCR for lubricant base oils having about the same ISO viscosity should be fairly linear since a predicted viscosity increase caused by increasing DMR should be mitigated or partially mitigated by a viscosity decrease predicted by increasing HCR. Accordingly, it can be seen in FIG. 8 that a plot of DMR and HCR for fluids having similar viscosities (from 49 cS to 58 cS) is fairly linear.

Comparing Experiment 2 to Experiment 1 in Table D, similar ISO viscosities were obtained by simultaneously raising both the DMR and HCR values of simulated ozone acids. The product obtained from Experiment 3 versus Experiment 2 illustrates the increased ISO viscosity obtained when the polyol DMR is increased without increasing the HCR while Experiment 4 versus Experiment 3 illustrates the decreased ISO viscosity obtained when increasing HCR without increasing the DMR. Lubricant base oil candidates obtained in Experiments 5-7 did not incorporate any nonanoic acid so the DMR of the materials reflects the inherent DMR of ozone acids without modification. The polyols in Experiments 5-7 were generated under conditions generating maximum amounts of cross-linking and potential gel formation. As evidence that the compositions were close to the gel point, very small amounts of gel needed to be filtered to obtain clear solutions. However, the filtered solutions were well-behaved and again illustrate the inverse dependence of ISO viscosities on HCR values. The relatively high ISO viscosity lubricant base oil candidates have much lower pour points than typically observed in competing higher viscosity lubricant base oils.

Also shown in Table D is Experiment 8 where a relatively high viscosity material was obtained when using a moderately high DMR and low NCR to obtain an ISO viscosity of 236 cS. This material had a relatively low pour point of −30° C. and this property combined with its high viscosity could make this material a good candidate for a gear oil or grease base stock. The above results indicate that a range of increased ISO viscosity gear and grease base stock candidates may be produced by simultaneous increases in DMR and HCR values of ester polyols produced from the esterification of ozone acids with TMP.

As shown in Table D, lubricant base oil obtained by simultaneously increasing both DMR and HCR can have reduced materials cost while obtaining similar ISO viscosities. A major factor in generating reduced material costs is that increased amounts of relatively non-purified ozone acids are assumed to be lowest cost components are incorporated under these conditions. The reason for this effect is that increased DMR values are obtained by adding lower amounts of additional monoacids, such as, nonanoic acid to simulated ozone acid mixtures that results in increased ozone acid percentages. D illustrates this trend while providing DMR and HCR data for a series of lubricant base oil candidates produced from the above stated reactions.

TABLE E

Effects of Partial Capping on Properties of Ester Polyol Esters and their Hydrolytic Stability
Effect of Partial Ester Polyol Capping on Ester Polyol Ester Properties and Hydrolytic Stability

| Lubricant | Intermediate Ester Polyol | | | | | Lubricant (Ester Polyol Ester) | | | | Hydrolytic Stability by ASTM D2619 | | | |
|---|---|---|---|---|---|---|---|---|---|---|---|---|---|
| LRB 52921- | Composition | DMR | HCR | HV | Capping Acid | % Capping | Viscosity @ 40° C. | VI | Pour Pt. (° C.) | Change in Acid No. | Water Total Acidity | Wt. Cu Panel mg/cm² | % Change in 40° C. Vis. (cS) |
| 43-28 | TMP, PFAD[a], | 0.11 | 1.25 | 87 | Non. A. | 100% | 37.7 cS | 157 | −48 | — | — | — | — |
| | | | | | | | | | | Not enough material was prepared to perform | | | |

TABLE E-continued

Effects of Partial Capping on Properties of Ester Polyol Esters and their Hydrolytic Stability
Effect of Partial Ester Polyol Capping on Ester Polyol Ester Properties and Hydrolytic Stability

| Lubricant | Intermediate Ester Polyol | | | | Lubricant (Ester Polyol Ester) | | | | Hydrolytic Stability by ASTM D2619 | | | |
| --- | --- | --- | --- | --- | --- | --- | --- | --- | --- | --- | --- | --- |
| LRB 52921- | Composition | DMR | HCR | HV | Capping Acid | % Capping | Viscosity @ 40° C. | VI | Pour Pt. (° C.) | Change in Acid No. | Water Total Acidity | Wt. Cu Panel mg/cm² | % Change in 40° C. Vis. (cS) |
| 68-30 | Non. A.[b] Same as above | 0.11 | 1.25 | 87 | Non. A. | 62% | 34.4 cP 42.1 cS 39.0 cP | 144 | −51 | hydrolytic stability tests Not enough material was prepared to perform hydrolytic stability tests | | | |
| Repeat Preparation of Above 2 Lubricants. | | | | | | | | | | | | | |
| 103-29 (Repeat of 43-28) | TMP/ PFAD[a], Non. A.[b] | 0.11 | 1.25 | 109 | Non. A. | 100% | 32.8 cP | — | — | +0.26 | 3.11 | −0.033 | −2.44 |
| | | | | | | | | | | Not enough material was prepared to perform pour point and viscosity (cS) tests | | | |
| 104-31 (Repeat of 68-30) | Same as above | 0.11 | 1.25 | 109 | Non. A. | 76% | 35.1 cP | — | — | +0.14 | 2.07 | −0.017 | −1.98 |
| | | | | | | | | | | Not enough material was prepared to perform pour point and viscosity (cS) tests | | | |

[a]PFAD: simulated fractionated PFAD ozone acids with DMR = 0.71;
[b]Non. A.: Nonanoic acid Table E illustrates the effects of partial capping of ester polyols on properties of the resulting mixtures of ester polyols and ester polyol esters. Capping ester polyols with less than 100 percent capping acids should result in lower cost lubricant basestocks due to lower amounts of monoacids needed for capping. Data shown in Table 9 shows select physical properties and performance properties of partially capped and fully capped ester polyols. The ester polyols were prepared from simulated ozone acids derived from PFAD with DMR and HCR values of 0.11 and 1.25, respectively and the preparations had to be re-prepared since insufficient material was available to perform all required tests. Following are some differences in test properties between fully capped and partially capped materials (capping percentage: 62%-76%). It can be seen that the incompletely capped lubricant candidates had slightly higher ISO viscosity, slightly lower pour point, and slightly increased stability in four hydrolytic stability tests prescribed by ASTM D2619 (Change in acid number, water total acidity, weight copper panel dissolution, and percent changes in 40° C. viscosity). Thus, it can be seen that incomplete capping can provide physical properties that are comparable to the fully capped ester polyol ester while also providing somewhat enhanced hydrolytic stability compared to the fully capped ester polyol esters. Accordingly, these incompletely capped ester polyols showed they had appreciably greater tendencies to produce lasting emulsions when vigorously shaken with water compared to fully capped ester polyols. Nevertheless, certain lubricant applications could benefit from the decreased materials cost of these basestocks while also benefiting from their increased hydrolytic stability.

TABLE F

Effects of Variations in Monoacids, Primary Polyols and Capping Acids on Ester Polyol Ester Properties
Variations in Monoacids, Primary Polyol and Capping Acids on Ester Polyol Ester Properties

| | Intermediate Ester Polyol | | | | Lubricant (Ester Polyol Ester) | | |
| --- | --- | --- | --- | --- | --- | --- | --- |
| Exp. No. | Composition | DMR | HCR | HV | Capping Acid | Viscosity @ 40° C. (cS) | Pour Point (° C.) |
| 1 | TMP, PFAD[a], Nonanonic Acid | 0.133 | 1.25 | 79 | Nonanoic Acid | 44.2 | −57 |
| | | | | | Acetic A. | 44.7 | −51 |
| 2 | TMP, Ed. OL-72[b], Nonanoic Acid | 0.21 | 1.25 | 67 | Nonanoic Acid[e] | 61.4 | −48 |
| | | | | | Emery 1210[c,e] | 57.2 | −54 |
| 3 | TMP, Ed Ol-72[b], Nonanoic Acid | 0.40 | 2.0 | 299.3 | Nonanoic Acid | 49.4 | −54 |
| | | | | | Hexanoic Acid | 43.3 | −54 |
| 4 | TMP, PFAD[a], Emery 1210[c] | 0.133 | 1.25 | 92 | Nonanoic Acid | 39.1 | −54 |
| 5 | TMP, PFAD[a], Nonanoic Acid | 0.21 | 1.24 | 80 | Nonanoic Acid | 61.6 | −42 |
| 6 | TMP/2-Me-1,3-PG[d] (4:1), PFAD[a], Nonanoic Acid | 0.21 | 1.25 | 84 | Nonanoic Acid | 44.2 | −45 |

[a]PFAD represents the ozone acids expected from palm oil fatty acid distillate (12% palmitic acid, 1.5% myristic acid, 68% oleic acid, and 16% linoleic acid) which results in a DMR of 0.71
[b]Edenor OL-72 represents an ozone acid mixture expected from olein that had been purified to contain nominally 72 percent oleic acid and the specific composition that was simulated contained 75.6% oleic acid, 11.4% linoleic acid, 4.41% palmitic, 2.8% stearic acid and 4.5% myristic acid which resulted in ozone acids with a DMR of 0.762

TABLE F-continued

Effects of Variations in Monoacids, Primary Polyols and
Capping Acids on Ester Polyol Ester Properties
Variations in Monoacids, Primary Polyol
and Capping Acids on Ester
Polyol Ester Properties

| | | | | | | Lubricant (Ester Polyol Ester) | |
|---|---|---|---|---|---|---|---|
| | Intermediate Ester Polyol | | | | | Viscosity @ 40° C. (cS) | Pour Point (° C.) |
| Exp. No. | Composition | DMR | HCR | HV | Capping Acid | | |

$^c$Emery 1210 is a commercially available mixture of monoacids (hexanoic acid, heptanoic acid, octanoic acid, and nonanoic acid in a 25:25:12:28 ratio) added to reduce the DMRs of ozone acids to desired values
$^d$2-Me-1,3-PG represents 2-methyl-1,3-propylene glycol which was added as a primary polyol in combination with TMP
$^e$Capping was performed with the acid chlorides of nonanoic acid and Emery 1210 since hexanoic acid in Emery 1210 was found to undergo azeotropic distillation during water distillation when driving esterifications to completion (not an issue when using acid chlorides for ester polyol capping)

Table F illustrates variations in ester polyol ester properties obtained in the two-step process when different monoacids are used to reduce the DMR of the ester polyol and also for capping purposes as well as when select additional primary polyols are use. In experiment 1, it can be seen that use of acetic acid as the capping acid in replacement of nonanoic acid leads to almost the same ISO viscosity and only a moderate reduction in ester polyol ester pour point. Substitution of acetic acid for nonanoic acid can have favorable economic impact due to it much lower molecular weight compared to nonanoic acid. In experiment 2, capping with Emery 1210, a commercially available mixture of $C_6$-$C_9$ monoacids, provides an alternate means to provide a moderate decrease in ester polyol ester viscosity and pour point (in addition to variations in DMR and HCR as previously demonstrated). Mixtures of monoacids are generally less expensive than pure acids so use of Emery 1210 is also expected to provide an economic advantage. Likewise, experiment 3 data illustrates that capping with hexanoic acid rather than nonanoic acid can be also be used to reduce the viscosity of ester polyol esters. Comparison of data in experiment 4 versus experiment 1 indicates that when Emery 1210 monoacids are substituted for nonanoic acid in preparing intermediate ester polyols (when capping with nonanoic acid) the ester polyol ester has a decreased ISO viscosity. Comparison of experiments 5 and 6 shown that substituting 20 mole percent of the primary polyol TMP with the branched diol 2-methyl-1,3-propylene glycol results in a very significant reduction in viscosity while also demonstrating a small decrease in pour point. This viscosity reduction probably resulted from the combined effect of introducing another branched primary polyol and also partial substitution of a triol (TMPM) with a diol, resulting in reduced crosslinking. These results demonstrate that another means of decreasing the viscosity of ester polyol esters is by partial or full replacement TMP with difunctional branched primary polyols.

Having now generally described the invention, the same will be more readily understood through reference to the following examples which are provided by way of illustration, and are not intended to be limiting of the present invention.

EXAMPLES

Example 1

This example is representative of the ester polyol ester (LRB 52921-101-21) produced from the ozone acids expected from the oxidative ozonolysis of fractionated PFAD. These simulated ozone acids from normal fatty acid distribution of fractionated PFAD were esterified with TMP with the addition of additional hexanoic acid to adjust the DMR to 0.05. The reactants were mixed in the round bottom flask fitted with a gas inlet tube fitted with a gas dispersing block, a Vigareux distillation column fitted with a cooled condenser and collection flask to collect distilled water. The mixture was initially homogenized at 100° C. using mechanical stirring. The temperature was increased to 160° C. to activate the catalyst. Water generated during esterification process was collected in the receiver flask. The temperature was then increased to 210° C. for several hours until the rate of water generated was low. In order to drive the esterification to near completion, inert gas (such as argon or nitrogen) was sparged into the reaction mixture at a rate of 0.5 SCFH. The reaction was deemed complete when the acid value (AV) was less than 1 mg KOH/g. The AV and hydroxyl value (HV) of the ester polyol was simultaneously determined by phosphorus NMR spectroscopy after initial derivitization of hydroxyl groups with 2-chloro-4,4,5,5-tetramethyldioxaphospholane as described by A. Spyros (J. Appl. Polym. Sci. 2002, 83, 1635). The required amount of capping acid to be added is dependent on the HV of the ester polyols.

The ester polyols are then esterified or capped with Emery 1210 carboxylic acids to generate ester polyol esters. In Example 1, the viscosity is 18.96 cSt at 40° C., which was significantly lower than examples using a higher DMR. A lower DMR resulted in decreased ester polyol ester molecular weights, resulting in decreased viscosity and increased volatility.

Example 2: (2-Step Process Using Tallow Based Ozone Acids

Step 1
  Azelaic acid (Emery 1110): 28.54%
  Pelargonic acid (Emery 1202): 35.69%
  TMP: 35.77%
  Catalyst: 0.06%
Step 2
  Pelargonic acid (Emery 1202): 46.8%
  Catalyst: 0.06%

The reactants were mixed in the round bottom flask fitted with a gas inlet tube fitted with a gas dispersing block, a Vigareux distillation column fitted with a cooled condenser and collection flask to collect distilled water. The mixture was initially homogenized at 100° C. using mechanical stirring. The temperature was increased to activate the catalyst. The temperature was then increased to 180° C. and subsequently to 210° C. In order to drive the esterification to near completion, inert gas was sparged into the reaction mixture at a rate of 0.5 SCFH. The reaction was deemed complete when the acid value (AV) was less than 1 mg KOH/g. The ester polyols are then esterified or capped with Emery 1202 carboxylic acids to generate ester polyol esters.

Result

| No | Description | Unit | Method | Polyol Ester LB25 |
|---|---|---|---|---|
| 1 | Appearance | — | Visual | B&C |
| 2 | Kinematic Viscosity, 40° C. | ° C. | ASTM D445 | 43.399 |
| 3 | Kinematic Viscosity, 100° C. | ° C. | ASTM D445 | 8.864 |
| 4 | Viscosity Index | — | ASTM D2270 | 154 |

-continued

| No | Description | Unit | Method | Polyol Ester LB25 |
|---|---|---|---|---|
| 5 | Colour | — | ASTM D1500 | L0 |
| 6 | Total Acid Number | mgKOH/g | ASTM D664 | 0.5 |
| 7 | Pour Point | ° C. | ASTM D97 | −54 |
| 8 | Flash Point | ° C. | ASTM D92 | >250 |

One-Step Conversion of Ozone Acids to Polyol Esters

An alternative embodiment to the two-step approach of converting ozone acids to polyol esters is the one-step approach of the present invention. In the one-step approach, the ozone acids, optional additional monoacids, and primary polyol are all added together and reacted at the same time. The one-step approach is illustrated in FIG. 9. The one-step approach avoids the capping step of the two-step approach by incorporating extra monoacid at the beginning of the reaction to obtain similar compositions and properties of these compositions as in the two-step process.

However, the two-step process can have significant advantages over the one-step conversion not only in the composition and performance of the resulting base oil but also in reduced reaction times. In the two-step process, the first reaction is performed with excess hydroxyl groups to prepare an ester polyol and the second step is generally performed with excess capping acid. Since each individual esterification step is run with excess reagent (hydroxyl groups in the first step and carboxylic acid groups in the second), the overall esterification reactions go to completion much more rapidly than the total reaction time of the analogous one-step process. Using this two-step process, lubricant base oil compositions were made with excellent pour points (below −35° C.) and a range of viscosities from quite low (<ISO 25) to high (>ISO 100). In testing of the lubricant, the materials had good wear characteristics and compositions prepared from both glycerin and TMP as primary polyols were determined to be fully biodegradable.

A compositional difference between the two methods is that in the first step of the two-step process, the primary polyol (typically trifunctional TMP) has a significantly greater amount of diacids compared to monoacids to react with compared to this ratio in the one-step process. By contrast, TMP molecules in the one-step process are inherently exposed to higher concentrations of monoacids during the entire reaction. Hence, in the one-step reaction it is expected that TMP molecules will undergo increased reaction with monoacids to form TMP tri(monofunctional acid) esters [TMP(O$_2$CR)$_3$] while also undergoing decreased chain extension and crosslinking caused by reaction of TMP with difunctional azelaic acid. Since TMP tri(monofunctional acid) esters would be the lowest molecular weight and most volatile of all species formed in the reactions, it would be expected that products from the two-step process would have higher molecular weight and decreased volatility compared to those generated from the one-step process.

In a comparison of the two-step vs. one-step esterification process, the DMR was varied where the DMR was 0.21, 0.40, and 0.50. In the comparative set of experiments where the DMR was 0.21 and the HCR was 1.24, the one-step product had a shift to lower molecular weight components based on gel permeation chromatography (GPC). This product also had a 17° C. lower volatilization onset temperature (based on scanning TGA to determine lubricant relative volatilities) that indicates the presence of more volatile components.

In two other comparisons where the DMR was either 0.4 or 0.5, the properties of the two-step and the one-step products were similar, with the two-step product having slightly decreased pour points and viscosities. However, based on the reaction considerations provided above, one would expect the product differences between the two-step and the one step to moderate with increasing DMR since decreased amounts of monoacids would be present in the higher DMR cases that cause differentiation between product compositions obtained from the two processes.

Another reaction characteristic that can favor the two-step process versus the one-step process is their total reaction (esterification) times. As shown in Table G, three comparative experiments were performed to test the differences between the two-step process and one-step process with the following combined DMR and HCR values: DMR 0.21, HCR 1.24 (Lubricants 1A and 1B); DMR 0.50, HCR 1.25 (Lubricants 2A and 2B); and DMR 0.40, HCR 2.00 (Lubricant 3A and 3B) as shown in Table G. Inspection of this data shows there is little difference in total esterification times between corresponding two-step and one-step reactions when comparing lubricants 1A and 1B and 2A and 2B. However, we believed that significant reduction in total esterification times would be more evident in the two-step process when higher HCR values were used since esterification rates under these conditions would benefit kinetically from the presence of a higher excess of hydroxyl functionality in the first esterification step and also from the presence of excess carboxylic acid functionality in the second step of the two-step process. In accordance with these expectations, it can be seen in Table G that the total esterification time to prepare lubricant 3A was significantly lower that the esterification time required to prepare lubricant 3B. The total esterification reaction time needed to produce lubricant 3A in the prescribed two-step process was 60 percent of the time needed to produce lubricant 3B in a one-step process under very similar reaction conditions. Both the two-step and one-step esterification reactions are typically catalyzed by tin oxalate or tin oxide catalysts and excess monoacids used in the last esterification reaction of the two-step process are removed by vacuum distillation or steam deodorization. Since distillation or deodorization to remove excess monoacids used in the second step will be performed in a separate reactor, this time is not counted in assessing reaction time. This reduced reaction time associated with the two-step process at conditions of high HCR has favorable economic implications as shown in Table D. Thus a favorable approach to prepare a desired viscosity base oil is to couple the simultaneous increase of the DMR and HCR of the composition to achieve decreased esterification reaction times and also increased economic benefits.

Further, inspecting Volatilization TGA Onset Temperature and GPC Highest Peak data for Lubricant Numbers 1A and 1B indicates that at low DMR values (0.21), the two step process results in a base oil with lower volatility and higher MW (based on these TGA onset temperatures and GPC highest peak values) compared to the one-step process. It is expected that relative volatilities and molecular weights would trend this way at low DMR values but less so at higher DMR values (such as 0.40 and 0.50 where these parameters have not yet been measured).

TABLE G

Data on Two-Step versus One-Step Esterification of Ozone Acids
to Produce Lubricant Base Oil
Two-Step versus One-Step Esterification of Ozone Acids with
Emery Ozone Acids[a] to Produce Lubricant Base Oil

| Lubricant Number | Process and Characterization | | | | Base Oil Properties | | | | |
|---|---|---|---|---|---|---|---|---|---|
| | Process | DMR | HCR | Total Reaction Time (hr) | Volatilization TGA Onset Temp. (° C.) | GPC Highest Peak | Viscosity @ 40 C. (cS) | Pour Point (° C.) | |
| 1A | two-step | 0.21 | 1.24 | 16.0 | 311.5 | 1837 | TBD | TBD | |
| 1B | one-step | Footnote "b" | Footnote "b" | 15.5 | 292.0 | 1745 | TBD | TBD | |
| 2A | two-step | 0.50 | 1.25 | 25.5 | TBD | TBD | 236 | −30 | |
| 2B | one-step | Footnote "b" | Footnote "b" | 25.3 | TBD | TBD | 240 | −36 | |
| 3A | two-step | 0.40 | 2.00 | 7.25 | TBD | TBD | 53 | −54 | |
| 3B | one-step | Footnote "b" | 1.005 | 12.0 | TBD | TBD | 57 | −51 | |

Figure 10:
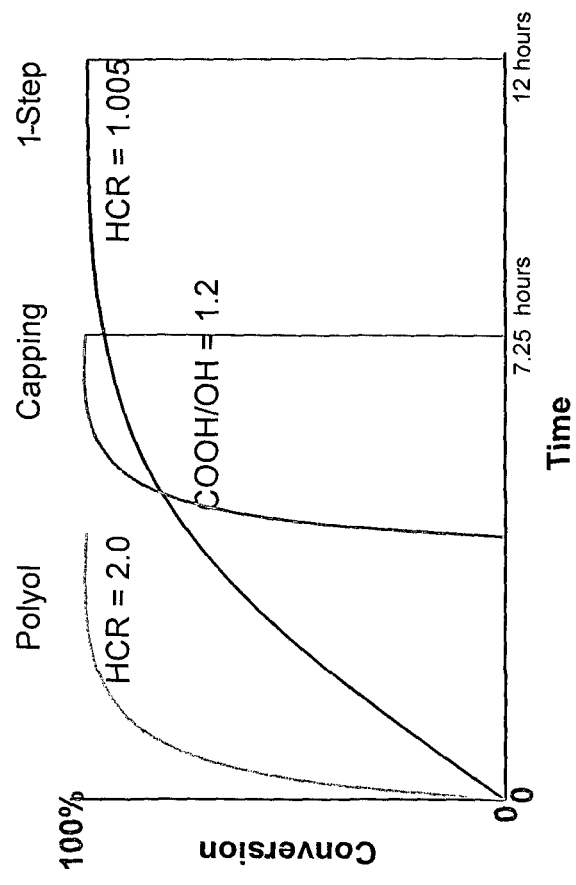
FIG. 10 is a graph illustrating the differences in reaction time and reactant concentration of the two-step synthesis versus the one-step synthesis of a ester polyol ester.

[a]Emerox 1110 (98% azelaic acid) and Emerox 1202 (95% nonanoic acid and the rest C8 and C10 diacids) were mixed to obtain stated DMR in two-step reactions.
[b]Compositions of one-step processes are the same as related two-step processes while adjusting the hydroxyl group concentrations to be about 0.5% in excess of total acid groups FIG. 10 graphically illustrates the improvement gained by the two-step conversion of ozone acids to polyol esters. The total esterification time for the two-step polyol ester was 7.25 hours. The HCR in this reaction was 2.0 and the esterification capping reaction had a carboxyl to hydroxyl ratio of 1.2 (and HCR ratio of 0.83). The HCR in the one-step approach was 1.005 and the esterification time was 12.0 hours. In this example, the total reaction time needed to produce the polyol esters of the two-step process was 40% less than the time needed to perform the one-step process.

The subject matter claimed herein is not limited to embodiments that solve any disadvantages or that operate only in environments such as those described above. Rather, this background is only provided to illustrate an exemplary technology area where some embodiments described herein may be practiced. Bibliographic references mentioned in the present specification are for convenience listed in the form of a list of references and added at the end of the examples. The whole content of such bibliographic references is herein incorporated by reference.

REFERENCES

1. WO 2010/078505
2. U.S. Pre-Grant Publication No. 2005/0112267
3. "The Preparation and Characterization of Trimethylolpropane Esters from Palm Kernel Oil Methyl Esters" (Robiah et al., *Journal of Oil Palm Research*, 15(2), December 2003, pp. 42-49)
4. Malaysian Patent No. 140833
5. U.S. Pat. No. 2,813,113
6. A. Spyros (J. Appl. Polym. Sci. 2002, 83, 1635).

The invention claimed is:

1. A method for preparing at least one ester polyol ester, the method comprising:

esterifying an ester polyol reaction mixture to produce ester polyol, the reaction mixture comprising at least one primary polyol selected from the group of trimethylolpropane ("TMP"), di-TMP, and 2-methyl-1,3-propanediol (2-MePG), and combinations thereof, and a mixture comprising (i) at least one dicarboxylic acid that is azelaic acid or a combination of azelaic and malonic acid, and (ii) at least one monocarboxylic acid that is selected from palmitic, stearic, myristic, hexanoic, heptanoic, octanoic, and nonanoic acids, and combinations thereof, wherein the mixture comprising at least one dicarboxylic acid and at least one monocarboxylic acid has a Difunctional/Monofunctional Ratio (DMR) corresponding to a ratio of moles of dicarboxylic acid to moles of monocarboxylic acid and the DMR is from about 0.05 to about 0.76; and capping the ester polyol with at least one capping carboxylic acid selected from hexanoic, heptanoic, octanoic, and nonanoic acids, acid chlorides formed therefrom, and combinations thereof, whereby said capping produces an ester polyol ester having a viscosity at 40° C. of from about 37.7 (cS) to about 236 (cS), and a pour point from about −57.0° C. to about −30.0° C.

2. The method according to claim 1, wherein:
(i) the mixture comprising at least one dicarboxylic acid and at least one monocarboxylic acid has a DMR from about 0.05 to about 0.71, and the ester polyol ester has a viscosity proportional to the DMR of the mixture; and/or
(ii) the ester polyol reaction mixture has a hydroxyl to carboxyl ratio (HCR) corresponding to a ratio of moles of OH groups to moles of COOH groups; where the HCR is from about 1.0 to about 2.0, and the ester polyol ester has a viscosity inversely proportional to the HCR of the ester polyol reaction mixture.

3. The method according to claim 1, wherein the mixture comprising at least one dicarboxylic acid and at least one monocarboxylic acid is prepared by reacting at least one fatty acid with ozone followed by oxidation.

4. The method according to claim 3, wherein the method comprises adding at least one additional second monocarboxylic acid to the mixture comprising at least one dicarboxylic acid and at least one monocarboxylic acid, wherein the first and second monocarboxylic acids are different.

5. The method according to claim 4, wherein said adding at least one additional second monocarboxylic acid reduces the Difunctional/Monofunctional Ratio (DMR) of the mixture comprising at least one dicarboxylic acid and at least one monocarboxylic acid.

6. The method according to claim 1, wherein the ester polyol reaction mixture comprises the at least one primary polyol in stoichiometric excess.

7. The method according to claim 2, wherein the ester polyol reaction mixture has a hydroxyl to carboxyl ratio (HCR) from about 1.01 to about 2.0.

8. The method according to claim 1, wherein the ester polyol ester has a viscosity proportional to the DMR of the mixture comprising at least one dicarboxylic acid and at least one monocarboxylic acid, and wherein the viscosity at 40° C. of the ester polyol ester is from about 39.1 (cS) to about 236 (cS).

9. The method according to claim 3, wherein
(a) the at least one fatty acid is derived from fractionated palm fatty acid distillate (PFAD);
the hydroxyl carboxyl ratio (HCR) of the ester polyol reaction mixture is about 1.25;

the Difunctional/Monofunctional Ratio (DMR) of the mixture comprising at least one dicarboxylic acid and at least one monocarboxylic acid is from about 0.11 to about 0.21;

the viscosity at 40° C. of the ester polyol ester is from about 37.7 (cS) to about 61.6 (cS);

and/or the ester polyol ester has a pour point from about −57.0° C. to about −42.0° C.;

(b) the at least one fatty acid is derived from palm kernel fatty acid distillate (PFKAD);

the Difunctional/Monofunctional ratio (DMR) of the mixture comprising at least one dicarboxylic acid and at least one monocarboxylic acid is about 0.12;

the hydroxyl carboxyl ratio (HCR) of the ester polyol reaction mixture is about 1.25;

and/or the viscosity at 40° C. of the ester polyol ester is about 53.7 (cS);

(c) the at least one fatty acid is derived from a mixture of fractionated palm fatty acid distillate (PFAD) and palm kernel fatty acid distillate (PFKAD);

the Difunctional/Monofunctional ratio (DMR) of the mixture comprising at least one dicarboxylic acid and at least one monocarboxylic acid is from about 0.05 to about 0.32;

the hydroxyl carboxyl ratio (HCR) of the ester polyol reaction mixture is about 1.25;

and/or the viscosity of the ester polyol ester is about 28 (cS) to about 120 (cS); or (d) the at least one fatty acid is derived from fractionated vegetable oleic acid;

the Difunctional/Monofunctional ratio (DMR) of the mixture comprising at least one dicarboxylic acid and at least one monocarboxylic acid is from about 0.13 to about 0.3;

the hydroxyl carboxyl ratio (HCR) of the ester polyol reaction mixture is about 1.25;

and/or the viscosity of the ester polyol ester is about 37.92 (cS) to about 96.13 (cS).

10. The method according to claim 1, wherein the primary polyol is 2-MePG or TMP.

11. The method according to claim 2, wherein a lubricant base stock is formed from the ester polyol ester; the lubricant base stock having a volatility inversely proportional to the DMR of the mixture comprising at least one dicarboxylic acid and at least one monocarboxylic acid.

12. The method according to claim 4, wherein the additional second monocarboxylic acid is selected from the group consisting of: acetic, propanoic, butyric, pentanoic, hexanoic, nonanoic, 2-ethyl hexanoic, heptanoic, octanoic, decanoic, lauric, myristic, palmitic and stearic acids, and mixtures thereof.

13. The method according to claim 3, wherein the at least one fatty acid is produced by hydrolyzing at least one triglyceride.

14. The method according to claim 13, wherein the at least one triglyceride comprises at least one vegetable oil, at least one animal fat, or a mixture thereof.

15. The method according to claim 1, wherein the capping step comprises using less than a stoichiometric amount of the at least one capping carboxylic acid.

16. The method according to claim 15, wherein the amount of the at least one capping carboxylic acid used is sufficient to achieve between about 62% to about 100% capping of the ester polyol.

17. A method for preparing an ester polyol ester, the method comprising:

esterifying a mixture comprising (i) at least one monocarboxylic acid that is selected from palmitic, stearic, myristic, hexanoic, heptanoic, octanoic, and nonanoic acids, and combinations thereof, and (ii) at least one dicarboxylic acid that is azelaic acid or a combination of azelaic and malonic acid, in the presence of at least one primary polyol selected from the group of trimethylolpropane (TMP) and 2-methyl-1,3-propanediol (2-MePG), and combinations thereof, wherein the method comprises adding to the mixture an additional monocarboxylic acid that is different from the at least one monocarboxylic acid, and wherein the ester polyol ester has a viscosity at 40° C. of from about 57 (cS) to about 240 (cS), and a pour point from about −51.0° C. to about −36.0° C.

18. The method according to claim 17, wherein the total amount of monocarboxylic acid is sufficient to achieve a substantially capped ester polyol ester.

19. The method according to claim 17, wherein the at least one monocarboxylic acid and the additional monocarboxylic acid are substantially completely esterified.

20. The method according to claim 17, wherein the total amount of the at least one primary polyol is in stoichiometric excess.

21. The method according to claim 17, wherein the at least one primary polyol is 2-MePG or TMP.

22. The method according to claim 1, wherein the ester polyol ester product obtained by said method has a viscosity at 40° C. of from about 37.7 (cS) to about 61.6 (cS), and a pour point from about −57.0° C. to about −42.0° C.

23. The method according to claim 1, wherein the ester polyol ester product obtained by said method has a viscosity at 40° C. of from about 37.7 (cS) to about 61.4 (cS), and a pour point from about −57.0° C. to about −48.0° C.

24. The method according to claim 17, wherein the additional monocarboxylic acid is selected from the group consisting of: propanoic, butyric, pentanoic, hexanoic, nonanoic, 2-ethyl hexanoic, heptanoic, octanoic, decanoic, lauric, myristic, palmitic and stearic acids, and mixtures thereof.

* * * * *

UNITED STATES PATENT AND TRADEMARK OFFICE
CERTIFICATE OF CORRECTION

PATENT NO. : 10,131,616 B2
APPLICATION NO. : 14/381545
DATED : November 20, 2018
INVENTOR(S) : Benecke and Garbark Page 1 of 1

It is certified that error appears in the above-identified patent and that said Letters Patent is hereby corrected as shown below:

In the Claims

Claim 2, Column 32, Line 33, delete "OH" and insert -- –OH -- in its place; and delete "COOH" and insert -- –COOH -- in its place.

Signed and Sealed this
Twelfth Day of March, 2019

Andrei Iancu
*Director of the United States Patent and Trademark Office*